United States Patent [19]

Obata et al.

[11] Patent Number: 5,717,481
[45] Date of Patent: Feb. 10, 1998

[54] PERIMETRIC MEASUREMENT APPARATUS FOR MEASURING CHARACTERISTICS OF X GANGLION CELLS

[75] Inventors: Nobusuke Obata; Satoru Niimura, both of Tokyo, Japan

[73] Assignee: Topcon Corporation, Tokyo, Japan

[21] Appl. No.: 546,074

[22] Filed: Oct. 20, 1995

[30] Foreign Application Priority Data

Oct. 20, 1994 [JP] Japan ................. 6-255554

[51] Int. Cl.$^6$ ................. A61B 3/02
[52] U.S. Cl. ............ 351/224; 351/226; 351/237
[58] Field of Search ................. 351/224, 225, 351/226, 222, 237, 239

[56] References Cited

U.S. PATENT DOCUMENTS

| | | | |
|---|---|---|---|
| 5,108,170 | 4/1992 | Sugiyama | 351/226 |
| 5,235,360 | 8/1993 | Minami | 351/226 |

OTHER PUBLICATIONS

Okamoto et al., "Characteristics of two systems of human vision using fundus perimetry," *Doc Ophthalmol Proceedings*, Series 49 (1986), pp. 483–488.

Anderson, *Automated Static Perimetry* (Mosby Year Book), pp. title and verso, vii–xii, 1–51, 68 & 69, 262,291, and 301–305 (1992).

Grüsser et al., *Visual Agnosias and Other Disturbances of Visual Perception and Cognition* (CRC Press, Inc.), pp. title and verso, v–ix, and 137–157 (1991).

Okamoto et al., "Review of visual system of human with an eye fundus perimeter," Neuro–ophthalmol. Jpn., vol. 3, No. 4 (1986).

Kani et al., "Visual field and receptive field," *Ophthalmology*, vol. 35, pp. 225–232 (1993).

Kani et al., "Fundus Controlled Perimetry," Docum. Ophthal. Proc. Series, vol. 19, pp. 341–350 (1979).

*Primary Examiner*—Huy Mai
*Attorney, Agent, or Firm*—Foley & Lardner

[57] ABSTRACT

An apparatus for measuring a visual field of a patient, especially characteristics of X ganglion cells, displays a series of targets to a patient. A ramp stimulus is used to measure characteristics of X ganglion cells. A target size setting device sets targets of various sizes. A stimulus intensity changing device changes the intensity of the stimulus in accordance with the size set by the target size setting device. A response device measures the response from the patient, that is, whether the patient senses the target. A memory stores the intensity of stimulus and target size corresponding to the patient's responses.

22 Claims, 21 Drawing Sheets

1 Half spherical dome
2 Projecting screen
3 Projecting optical system
4 Illuminating light
5 Condenser lens
6 Circular edge
7 Target board
8 Condenser lens
9 Focus lens
10a Reflection mirror
10b Reflection mirror
11 Guide hole

FIG.6

| size / position | -II | -I | 0 | I | II | III | IV | V |
|---|---|---|---|---|---|---|---|---|
| 0° | D1+6 | D1 | D1-7=D3 | D2-2=D4 | D2-2=D4 | D2 | D2 | D2 |
| 5° | D1-2 | D1-7 | D3-13 | D4-6 | D4-5 | D2 | D2 | D2 |
| 10° | D1-4 | D1-9 | D3-16 | D4-11 | D4-9 | D2 | D2 | D2 |
| 15° | D1-6 | D1-12 | D3-22 | D4-14 | D4-10 | D2 | D2 | D2 |
| 20° | D1-8 | D1-14 | D3-22 | D4-16 | D4-12 | D2 | D2 | D2 | unit is dB  D1=D10-3dB  D2=D20-3dB

| position | size: -I | size: 0 | size: I | size: II | size: III | size: IV |
|---|---|---|---|---|---|---|
| 0° | 2.346090 | 2.703276 | 3.083572 | 3.647906 | 4.246712 | 4.837404 |
| 5° | 2.934102 | 2.878962 | 3.232546 | 3.712249 | 4.271725 | 4.847058 |
| 10° | 3.027502 | 3.022016 | 3.274099 | 3.734324 | 4.284162 | 4.861932 |
| 15° | 3.217920 | 3.266751 | 3.432928 | 3.760608 | 4.317701 | 4.872071 |
| 20° | 3.411763 | 3.916559 | 3.497010 | 3.760608 | 4.299330 | 4.872071 |

($\alpha$ : pulse)

| position | size: -I | size: 0 | size: I | size: II | size: III | size: IV |
|---|---|---|---|---|---|---|
| 0° | 2.346090 | 2.547423 | 3.117111 | 3.635905 | 4.233612 | 4.833958 |
| 5° | 2.752338 | 2.814880 | 3.196448 | 3.678710 | 4.241358 | 4.841704 |
| 10° | 3.027502 | 3.100074 | 3.196448 | 3.693877 | 4.246712 | 4.853705 |
| 15° | 2.122188 | 3.181819 | 3.321324 | 3.827683 | 4.261585 | 4.853705 |
| 20° | 2.607833 | 3.266751 | 3.432928 | 3.791586 | 4.261585 | 4.847058 |

($\alpha$ : 10dB/8S)

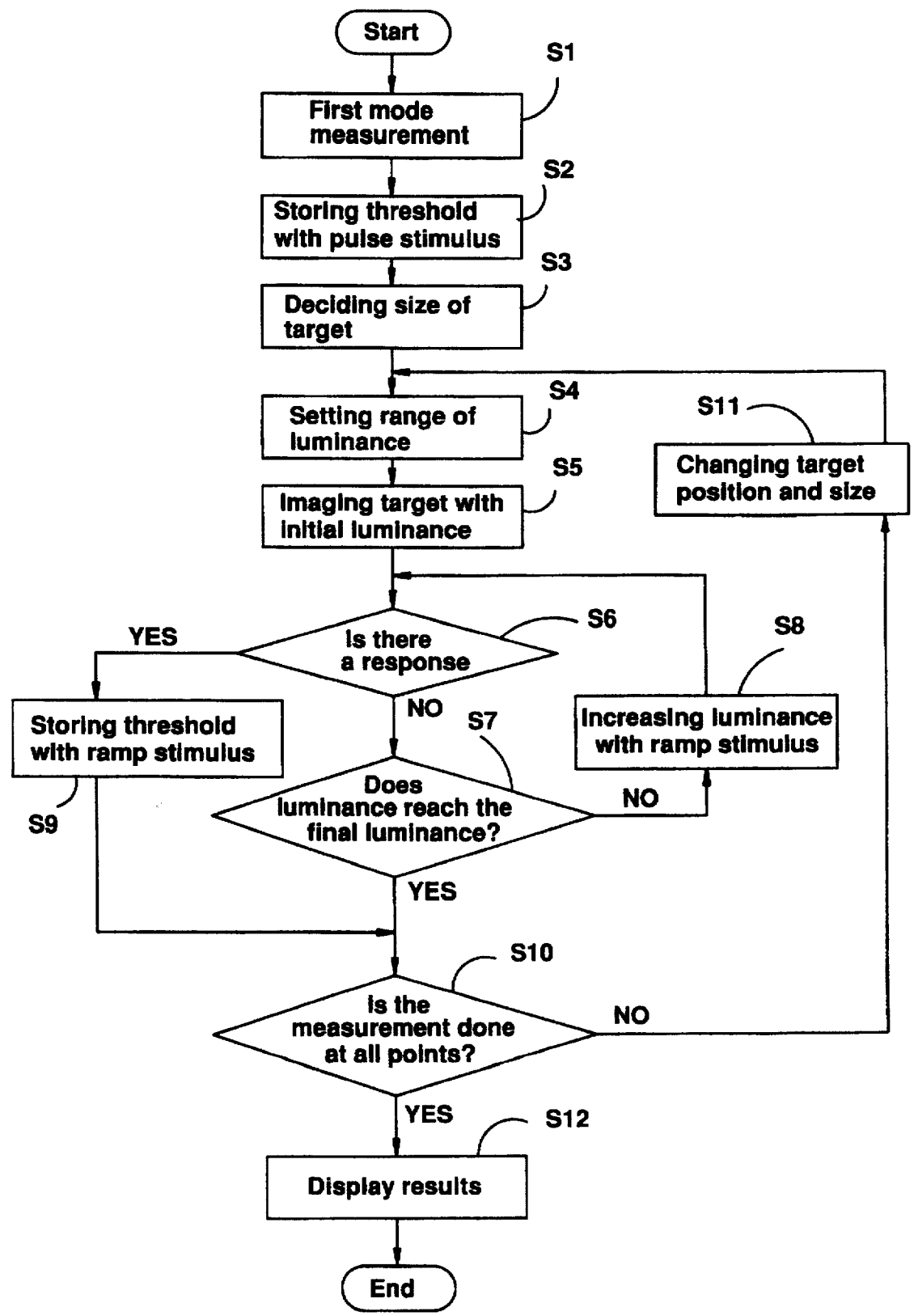

|  | size: −I | size: 0 | size: I | size: II | size: III | size: IV |
|---|---|---|---|---|---|---|
| 0° | 2.498014 | 2.703276 | 3.117111 | 3.693877 | 4.284162 | 4.872071 |
| 5° | 3.217920 | 2.444329 | 3.640064 | 3.827683 | 4.317701 | 4.884509 |
| 10° | 3.904453 | 3.916559 | 3.640064 | 4.161336 | 4.521914 | 4.940123 |
| 15° | 3.805335 | 3.629562 | 3.718122 | 4.092147 | 4.397038 | 4.966407 |
| 20° | 3.805335 | 3.819980 | 3.154210 | 4.092147 | 4.574883 | 4.940123 |

($\alpha$ : 30dB/4S)

|  | size: ㅍ | size: 0 | size: I | size: II | size: III | size: IV |
|---|---|---|---|---|---|---|
| 0° | 3.706442 | 3.181819 | 3.432928 | 3.827683 | 4.317701 | 4.966407 |
| 5° | 4.202749 | 3.819980 | 3.972446 | 4.235201 | 4.574883 | 4.940123 |
| 10° | 4.302396 | 4.209893 | 4.247610 | 4.842748 | 4.697600 | 4.966407 |
| 15° | 4.302396 | 3.819980 | 4.247610 | 4.395005 | 4.633518 | 4.997385 |
| 20° | 4.302396 | 4.308502 | 4.247610 | 4.749347 | 4.697600 | 4.075036 |

($\alpha$ : 30dB/2S)

| | size: I' | size: 0 | size: I | size: II | size: III | size: IV |
|---|---|---|---|---|---|---|
| 0° | 2.498014 | 2.656051 | 3.165471 | 3.678710 | 4.261585 | 4.853705 |
| 5° | 2.934102 | 2.948150 | 3.232546 | 3.712249 | 4.299330 | 4.861932 |
| 10° | 3.122188 | 3.100074 | 3.232546 | 3.760608 | 4.299330 | 4.872071 |
| 15° | 3.314499 | 3.444329 | 3.432328 | 3.827683 | 4.299330 | 4.881932 |
| 20° | 3.509577 | 3.536162 | 3.640064 | 3.827683 | 4.317701 | 4.872071 |

($\alpha$ : 30dB/8S)

| | size: ⊥ | size: 0 | size: I | size: II | size: III | size: IV |
|---|---|---|---|---|---|---|
| 0° | 2.498014 | 2.614498 | 3.165471 | 3.647906 | 4.271725 | 4.853705 |
| 5° | 2.934102 | 2.948150 | 3.321324 | 3.760608 | 4.299330 | 4.872071 |
| 10° | 3.314499 | 3.181819 | 3.566198 | 3.916462 | 4.339776 | 4.884509 |
| 15° | 3.314499 | 3.354398 | 3.566198 | 3.696430 | 4.433136 | 4.899676 |
| 20° | 3.904453 | 3.724248 | 3.566198 | 3.969430 | 4.366061 | 4.884509 |

(α : 30dB/10S)

| position | size: -I | size: 0 | size: I | size: II | size: III | size: IV |
|---|---|---|---|---|---|---|
| 0° | 2.212820 | 2.614498 | 3.098740 | 3.656138 | 4.248712 | 4.833958 |
| 5° | 2.664691 | 2.878962 | 3.232546 | 3.693877 | 4.299330 | 4.861932 |
| 10° | 3.122188 | 3.100074 | 3.374293 | 3.760608 | 4.317701 | 4.884509 |
| 15° | 3.607833 | 3.536162 | 3.799867 | 3.869237 | 4.339776 | 4.918048 |
| 20° | 3.607833 | 3.724248 | 3.566198 | 3.859237 | 4.339776 | 4.884509 |

(β: pulse)

|  | size: -I | size: 0 | size: I | size: II | size: III | size: IV |
|---|---|---|---|---|---|---|
| 0° | 3.805335 | 3.022016 | 3.566198 | 3.693877 | 4.366061 | 4.847058 |
| 5° | 3.904453 | 3.724248 | 3.640064 | 4.235201 | 4.521914 | 4.997385 |
| 10° | 4.103193 | 4.013823 | 4.342296 | 4.028065 | 4.574883 | 4.997385 |
| 15° | 4.302396 | 4.111637 | 4.247610 | 4.395005 | 4.633518 | 4.997385 |
| 20° | 4.302396 | 4.605811 | 4.154210 | 4.395005 | 4.633518 | 5.075036 |

($\beta$ : 30dB/2S)

|  | size: -I | size: 0 | size: I | size: II | size: III | size: IV |
|---|---|---|---|---|---|---|
| 0° | 2.419956 | 2.756245 | 3.165471 | 3.678710 | 4.253359 | 4.853705 |
| 5° | 3.217920 | 3.100074 | 3.374293 | 3.791586 | 4.317701 | 4.884509 |
| 10° | 3.314499 | 3.354398 | 3.884799 | 3.827683 | 4.366061 | 4.918048 |
| 15° | 3.805335 | 3.536162 | 3.718122 | 4.092147 | 4.397038 | 4.899676 |
| 20° | 3.706442 | 3.916559 | 3.799867 | 3.918462 | 4.433136 | 4.940123 |

($\beta$ : 30dB/4S)

|  | size: -I | size: 0 | size: I | size: II | size: III | size: IV |
|---|---|---|---|---|---|---|
| 0° | 2.346090 | 2.578400 | 3.052769 | 3.656133 | 4.261585 | 4.841704 |
| 5° | 3.027502 | 2.948150 | 3.321324 | 3.712249 | 4.271725 | 4.847058 |
| 10° | 3.217920 | 3.181819 | 3.374293 | 3.760608 | 4.317701 | 4.853705 |
| 15° | 3.607833 | 3.444329 | 3.718122 | 3.827683 | 4.317701 | 4.861932 |
| 20° | 3.706442 | 3.724248 | 3.640064 | 3.869237 | 4.317701 | 4.853705 |

($\beta$: 30dB/8S)

|  | size: -I | size: 0 | size: I | size: II | size: III | size: IV |
|---|---|---|---|---|---|---|
| 0° | 2.212820 | 2.703276 | 3.139186 | 3.647906 | 4.261585 | 4.853705 |
| 5° | 3.122188 | 3.100074 | 3.232546 | 3.734324 | 4.271725 | 4.853705 |
| 10° | 3.509577 | 3.444329 | 3.432928 | 3.827683 | 4.317701 | 4.853705 |
| 15° | 3.706442 | 3.629582 | 3.640064 | 3.827683 | 4.339776 | 4.918048 |
| 20° | 4.003751 | 3.536162 | 3.799867 | 3.969430 | 4.366061 | 4.918048 |

($\beta$ : 30dB/10S)

|  | size: -I | size: 0 | size: I | size: II | size: III | size: IV |
|---|---|---|---|---|---|---|
| 0° | 2.212820 | 2.499063 | 3.052769 | 3.641259 | 4.246712 | 4.837404 |
| 5° | 2.752338 | 2.878962 | 3.196448 | 3.712249 | 4.261585 | 4.841704 |
| 10° | 3.027502 | 3.266751 | 3.321324 | 3.760608 | 4.284162 | 4.853705 |
| 15° | 3.217920 | 3.354398 | 3.432928 | 3.791586 | 4.271725 | 4.881932 |
| 20° | 3.314499 | 3.354398 | 3.497010 | 3.827683 | 4.299330 | 4.881932 |

($\beta$: 10dB/8S)

PERIMETRIC MEASUREMENT APPARATUS FOR MEASURING CHARACTERISTICS OF X GANGLION CELLS

BACKGROUND OF THE INVENTION

1. Field of the Invention

This invention relates to a perimetric measurement apparatus for measuring characteristics of nerve cells in a patient's eye. More specifically, the invention relates to an apparatus for measuring characteristics of X ganglion cells in a patient's eye.

2. Background Information

A perimeter is a device used to make measurements of a patient's eye. The retina of a human eye contains two types of nerve cells—X ganglion cells and Y ganglion cells.

Recently, a few papers discuss measurement of characteristics of X ganglion cells. See, for example, "Characteristics of two systems of human vision using fundus perimetry" by Y. Okamoto, O. Mimura, K. Xani and T. Inui appearing in Doc Ophthalmol Proceedings, Series 49 (1986). However, the design of an acceptable apparatus for measuring characteristics of the X ganglion cells has not been reported.

There are more X ganglion cells than Y ganglion cells in the optic nerves. X ganglion cells occupy about 80% of the optic nerves. Because the X ganglion cells are slimmer than other optical nerves, defects such as glaucoma and the like tend to first appear at an area of X ganglion cells.

A prior perimetric measurement device is designed to measure characteristics of the Y ganglion cells with a pulse stimulus. However, such a perimetric measurement device does not adequately reveal defects at an early stage because the device provides characteristics of only the Y ganglion cells.

General background information on vision and perimetry is set forth in U.S. Pat. No. 5,108,170, issued on Apr. 28, 1992 to Akihiro Sugiyama; Automated Static Perimetry by Douglas R. Anderson, M.D. (Mosby Year Book); and Visual Agnosias and Other Disturbances of Visual Perception and Cognition by Otto-Joachim Grüsser and Theodor Landis (CRC Press, Inc.). The entire contents of these documents are expressly incorporated herein by reference.

SUMMARY OF THE INVENTION

An object of the invention is to provide an improved perimetric measurement apparatus that will detect eye problems at an early stage.

Another object of the present invention is to provide a perimetric measurement apparatus for measuring characteristics of X ganglion cells.

Another object of the present invention is to provide an apparatus for measuring characteristics of X ganglion cells using a first mode and a second mode of operation, wherein the first mode generates a pulse stimulus for the retina to measure a characteristic of the Y ganglion cells, and the second mode generates a monotonically-increasing or a ramp stimulus for the retina to measure a characteristic of the X ganglion cells. In the second mode, the apparatus generates an initial stimulus based on the response from the patient during the first mode.

A further object of the present invention is to provide an apparatus for measuring a characteristic of X ganglion cells, using a stimulus intensity changing device for changing the intensity of stimulus based on the position of a target generated by a target presenting device.

A further object of the present invention is to provide an apparatus for measuring a characteristic of X ganglion cells, using a stimulus intensity changing device for changing the intensity of stimulus based on the size of a target.

A further object of the present invention is to provide an apparatus for measuring a characteristic of X ganglion cells which employs a stimulus intensity changing device for changing the intensity of stimulus at a stimulus intensity changing rate which is slower than the response rate of Y ganglion cells and faster than a patient's fixation instability rate.

According to a first aspect of the invention, an apparatus is provided for measuring a visual field of a patient, especially characteristics of X ganglion cells.

The apparatus includes a target presenting device for presenting a target for viewing by the patient, which has a first mode and a second mode. The first mode generates a pulse stimulus to measure a characteristic of Y ganglion cells. The second mode generates a ramp stimulus to measure a characteristic of X ganglion cells. The apparatus also includes a response device for measuring the response of the patient. In the second mode, the apparatus generates an initial stimulus based on the response from the patient in the first mode.

According to a second aspect of the invention, an apparatus is provided for measuring a visual field of a patient, especially characteristics of X ganglion cells.

The apparatus includes a target size setting device for setting targets of various sizes and a stimulus intensity changing device for changing the intensity of stimulus based on the size set by the target size setting device. This apparatus also includes a response device for measuring the response of the patient and a memory for storing an intensity of stimulus and a target size corresponding to the patient's responses.

According to a third aspect of the invention, an apparatus is provided for measuring a visual field of a patient, especially characteristics of X ganglion cells.

The apparatus includes a target presenting device for presenting a target at desired positions and with a varying intensity of stimulus, a target size changing device for changing a size of a target which is generated by the target presenting device, and a stimulus intensity changing device for changing the intensity of stimulus based on the position of the target generated by the target presenting device. The apparatus also includes a response device for measuring the response of the patient and a memory for storing an intensity of stimulus and a target size corresponding to the patient's response.

According to a fourth aspect of the invention, an apparatus is provided for measuring a visual field of a patient, especially characteristics of X ganglion cells.

The apparatus includes a target presenting device for presenting a target at desired positions and with a varying intensity of stimulus, a stimulus intensity changing device for changing the intensity of stimulus based on the position and the size of the target generated by the target presenting device. The apparatus also includes a response device for measuring the response of the patient and a memory for storing an intensity of stimulus and a target size corresponding to the patient's responses. The stimulus intensity changing device changes the intensity of stimulus at a stimulus intensity changing rate which is slower than the response rate of the Y ganglion cells and faster than the patient's fixation instability rate.

BRIEF DESCRIPTION OF THE DRAWINGS

The invention will be described in further detail below with reference to the accompanying drawings, wherein:

FIG. 6 is a chart showing a starting luminance of a target.

FIG. (b) is a chart showing characteristic data of X ganglion cells of a patient α with ramp stimulus.

FIG. 10 is a flow chart of processing of perimetric measurements that are performed by another embodiment of this invention.

Figures 11A, 11B:
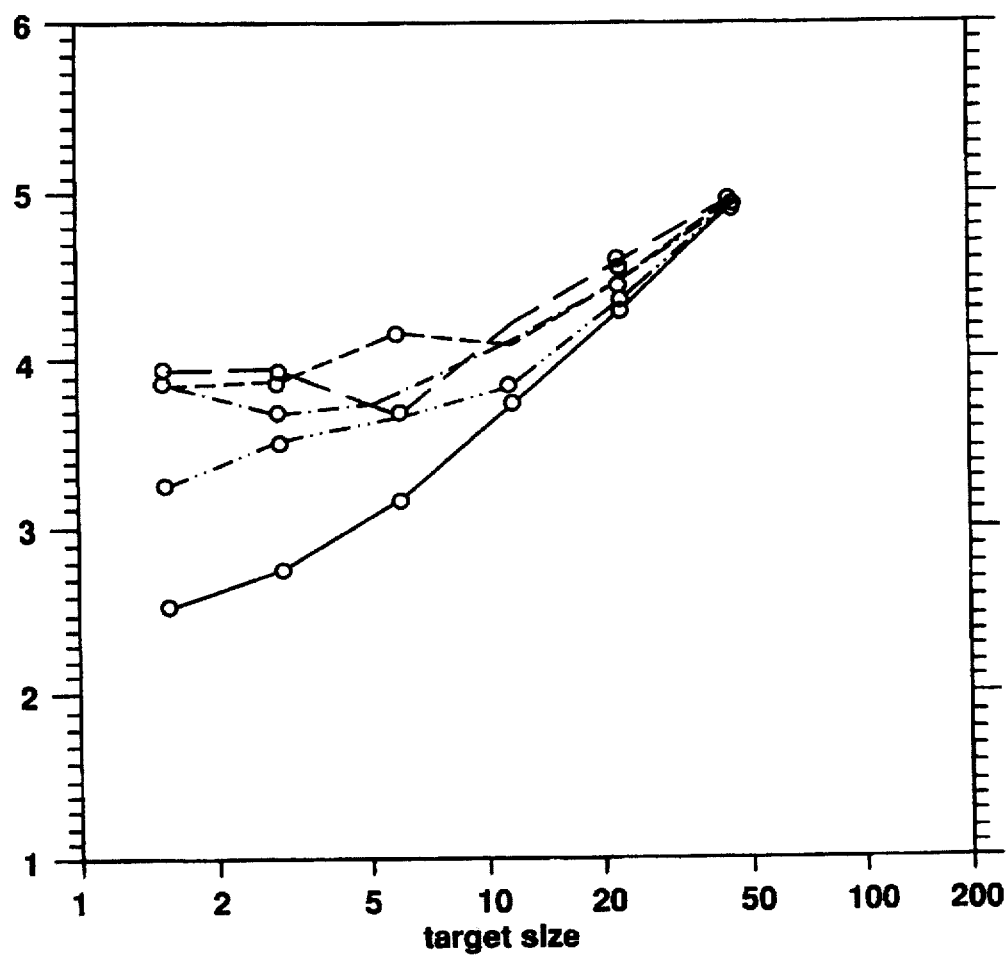

FIG. 11(a) is a graph showing characteristic of X ganglion cells of a patient α with ramp stimulus.

FIG. 11(b) is a chart showing characteristic data of Y ganglion cells of a patient α with ramp stimulus.

Figures 12A, 12B:
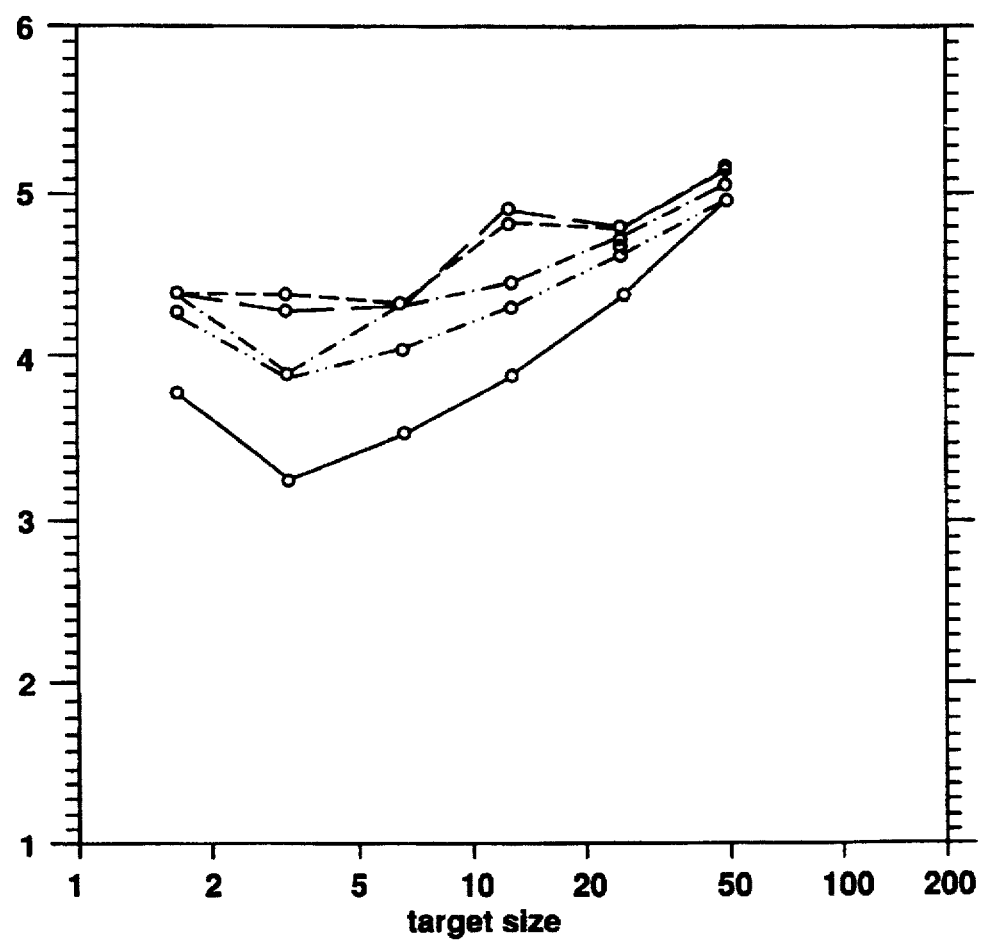

FIG. 12(a) is a graph showing characteristic of X ganglion cells of a patient α with ramp stimulus.

FIG. 12(b) is a chart showing characteristic data of X ganglion cells of a patient α with ramp stimulus.

Figures 13A, 13B:
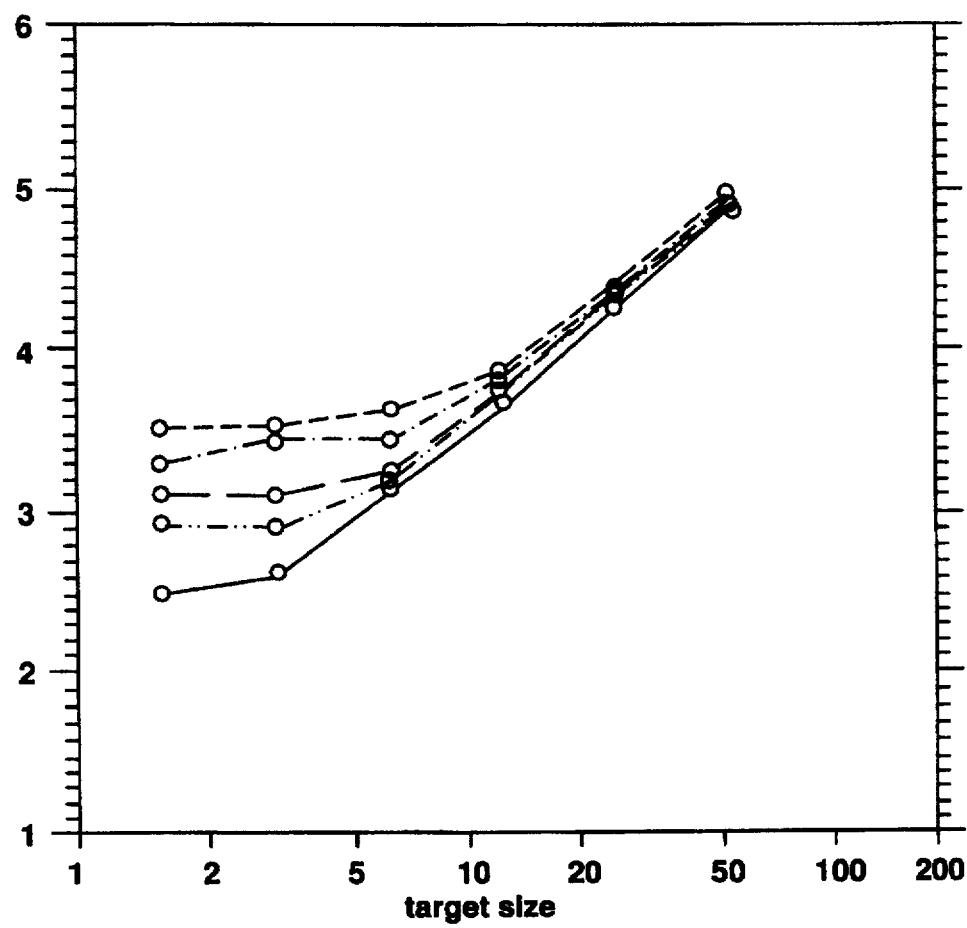

FIG. 13(a) is a graph showing characteristic of X ganglion cells of a patient α with ramp stimulus.

FIG. 13(b) is a chart showing characteristic data of X ganglion cells of a patient α with ramp stimulus.

Figures 14A, 14B:
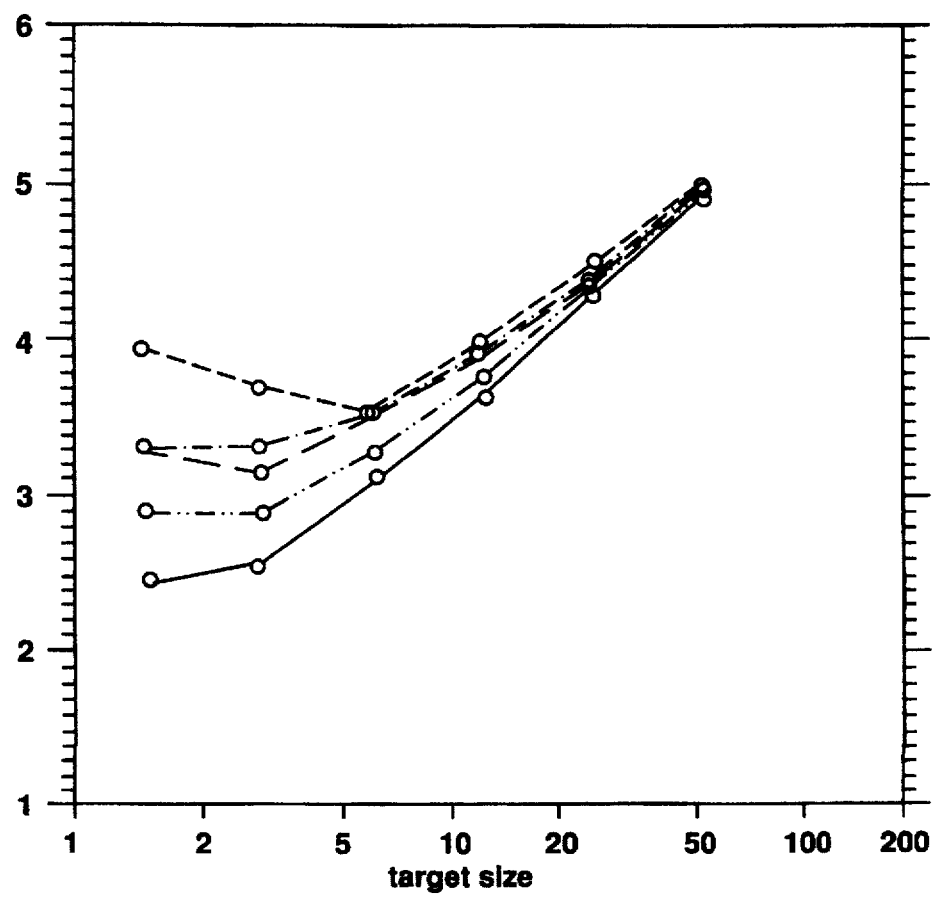

FIG. 14(a) is a graph showing characteristic of X ganglion cells of a patient α with ramp stimulus.

FIG. 14(b) is a chart showing characteristic data of X ganglion cells of a patient α with ramp stimulus.

Figures 15A, 15B:
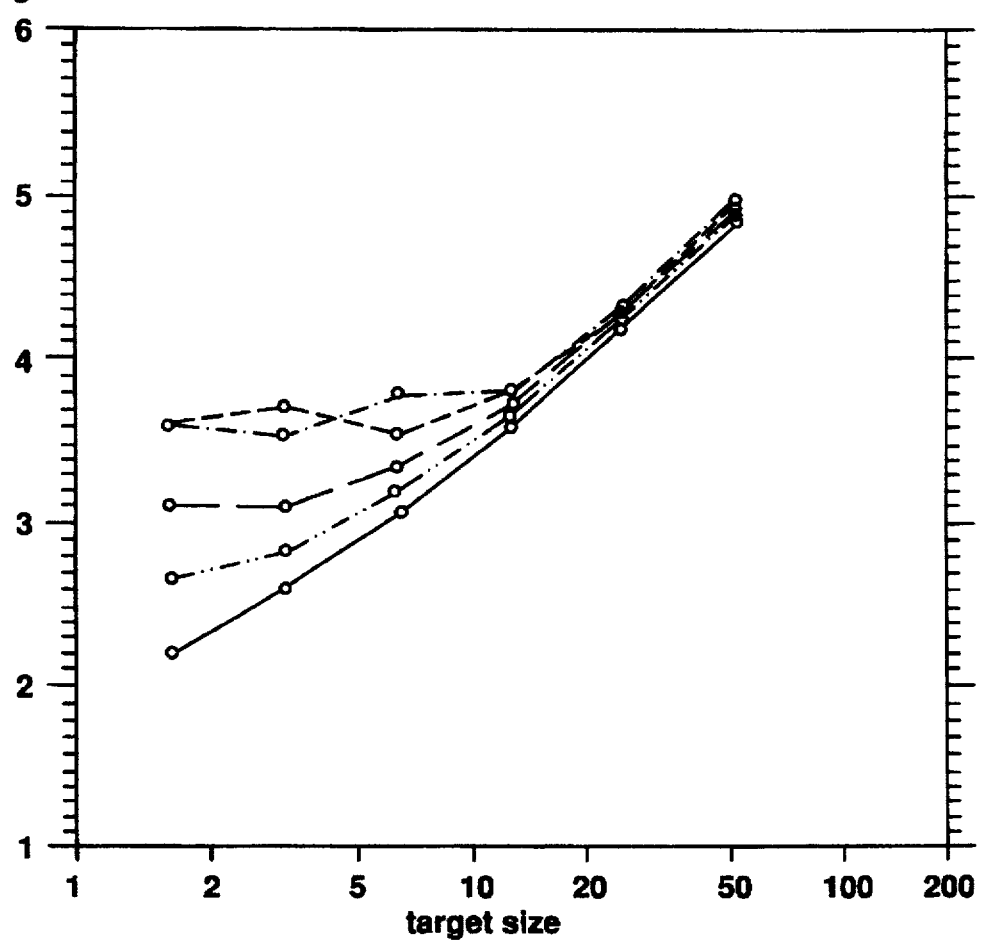

FIG. 15(a) is a graph showing characteristic of Y ganglion cells of a patient α with pulse stimulus.

FIG. 15(b) is a chart showing characteristic data of Y ganglion cells of a patient β with pulse stimulus.

Figures 16A, 16B:
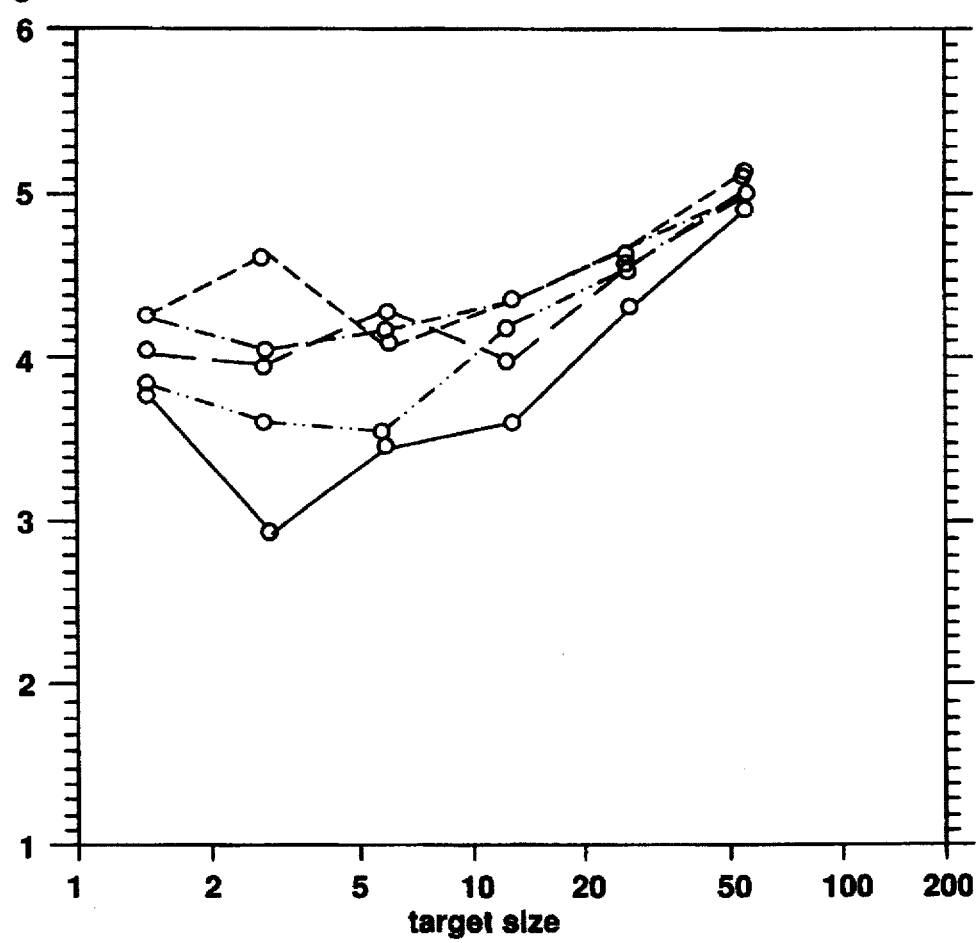

FIG. 16(a) is a graph showing characteristic of X ganglion cells of a patient β with ramp stimulus.

FIG. 16(b) is a chart showing characteristic data of X ganglion cells of a patient β with ramp stimulus.

Figures 17A, 17B:
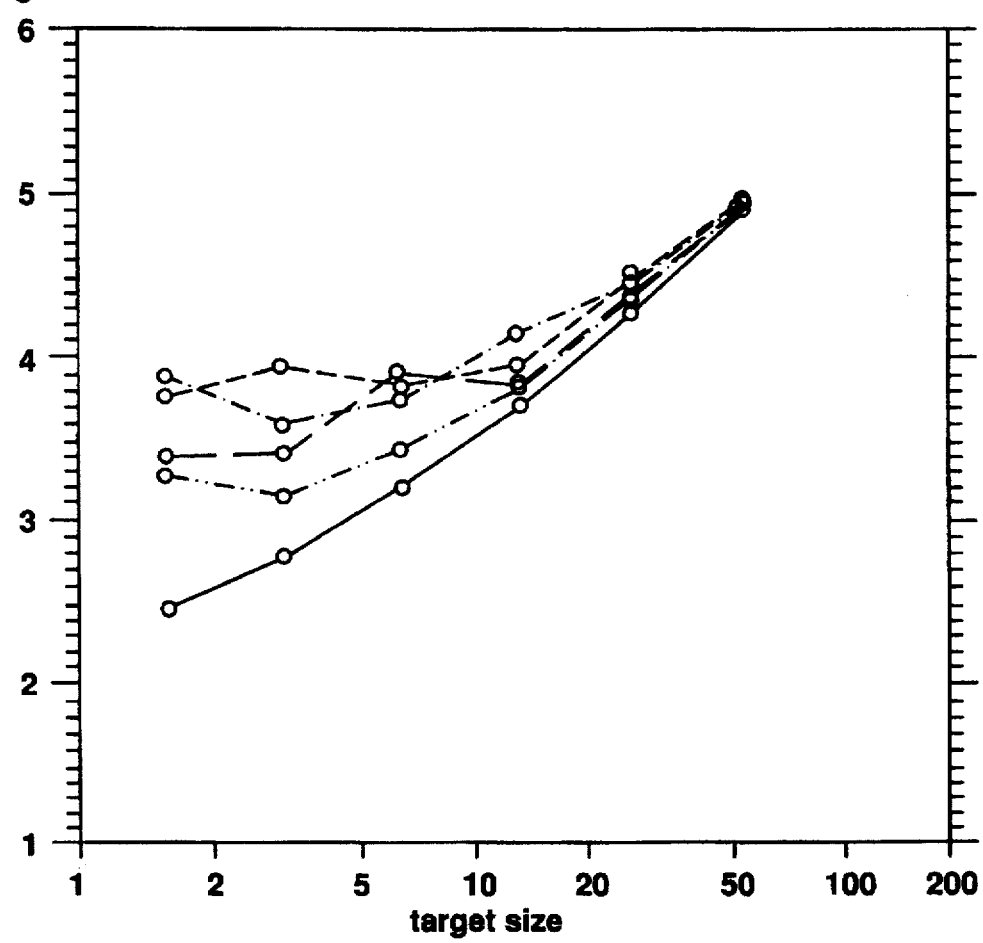

FIG. 17(a) is a graph showing characteristic of X ganglion cells of a patient β with ramp stimulus.

FIG. 17(b) is a chart showing characteristic data of X ganglion cells of a patient β with ramp stimulus.

Figures 18A, 18B:
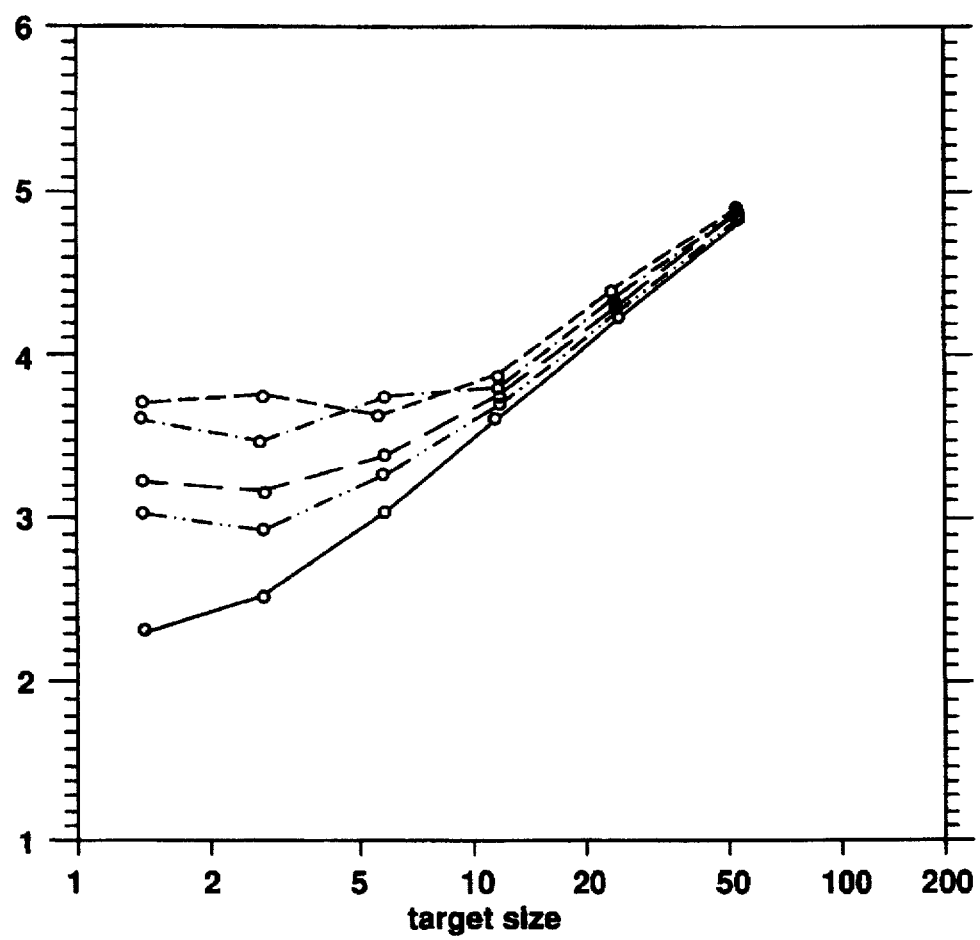

FIG. 18(a) is a graph showing characteristic of X ganglion cells of a patient β with ramp stimulus.

FIG. 18(b) is a chart showing characteristic data of X ganglion cells of a patient β with ramp stimulus.

Figures 19A, 19B:
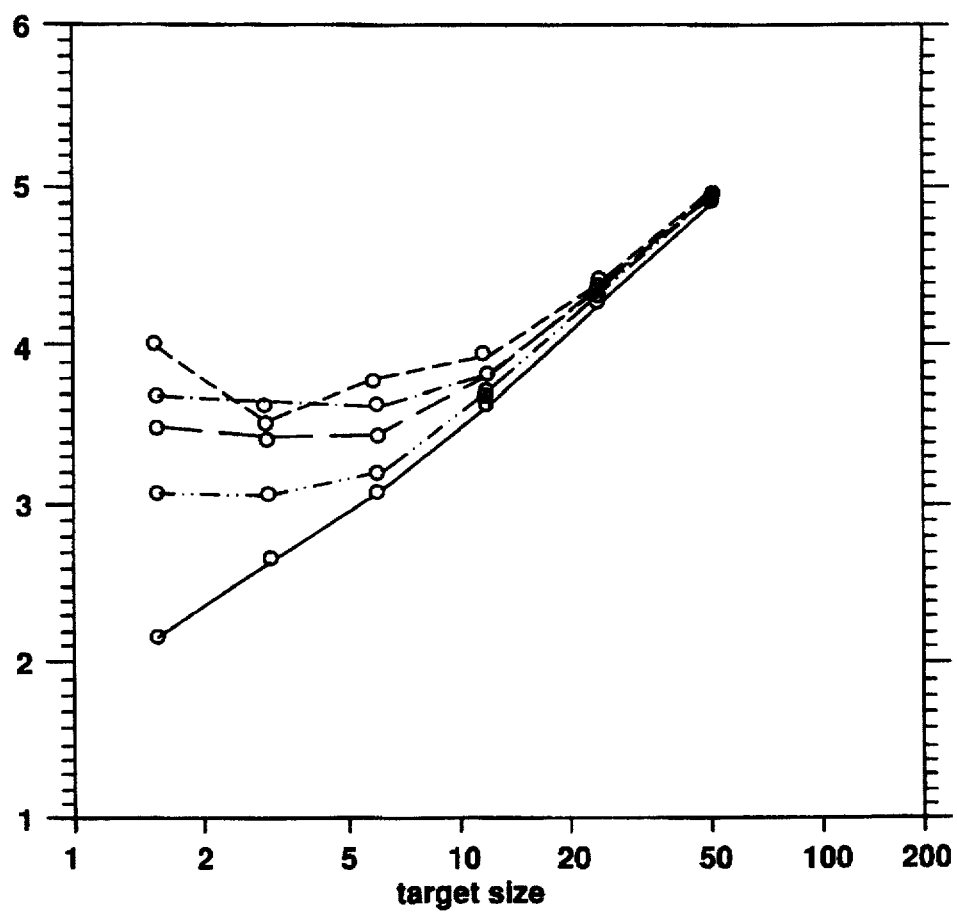

FIG. 19(a) is a graph showing characteristic of X ganglion cells of a patient β with ramp stimulus.

FIG. 19(b) is a chart showing characteristic data of X ganglion cells of a patient β with ramp stimulus.

Figures 20A, 20B:
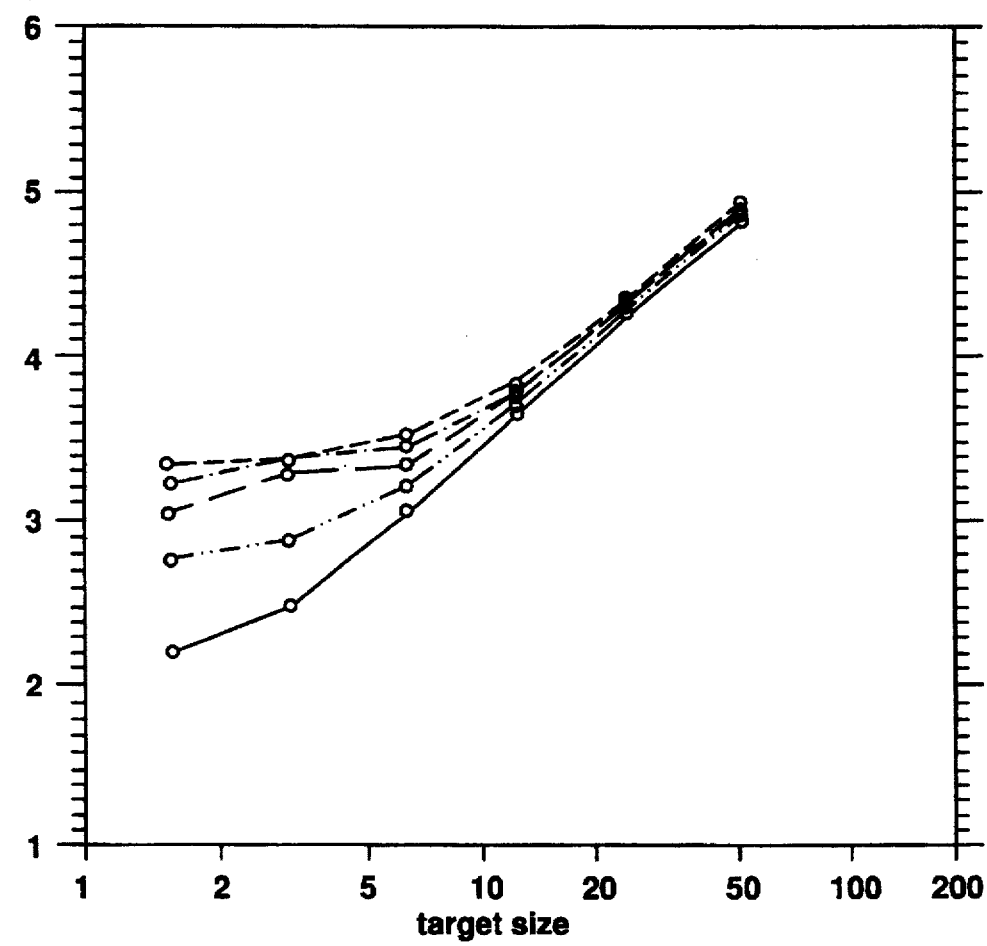

FIG. 20(a) is a graph showing characteristic of X ganglion cells of a patient β with ramp stimulus.

FIG. 20(b) is a chart showing characteristic data of X ganglion cells of a patient β with ramp stimulus.

Figure 21:
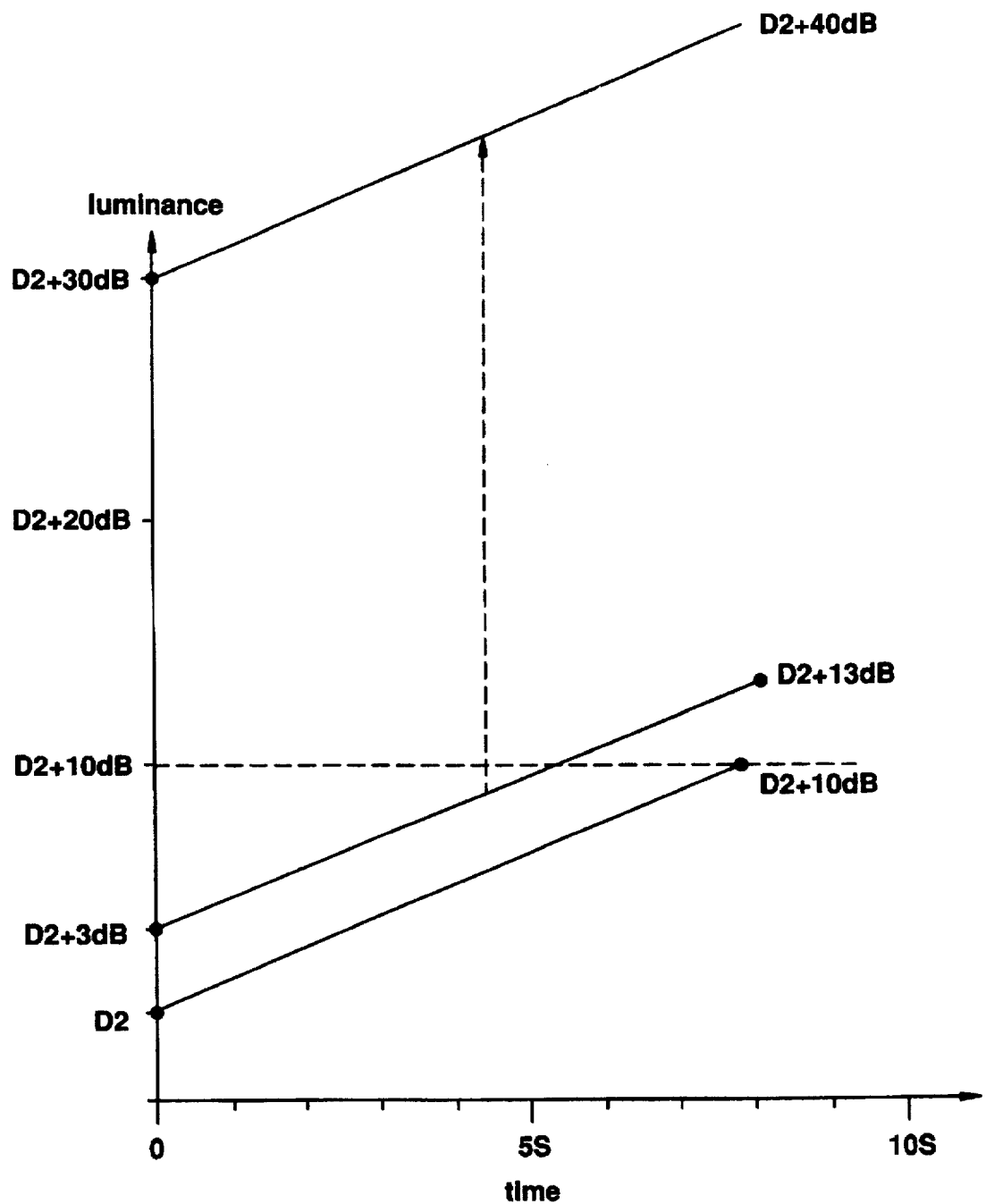

FIG. 21 is a graph showing a shift of a changing area.

DETAILED DESCRIPTION OF PREFERRED EMBODIMENTS

Figure 1:
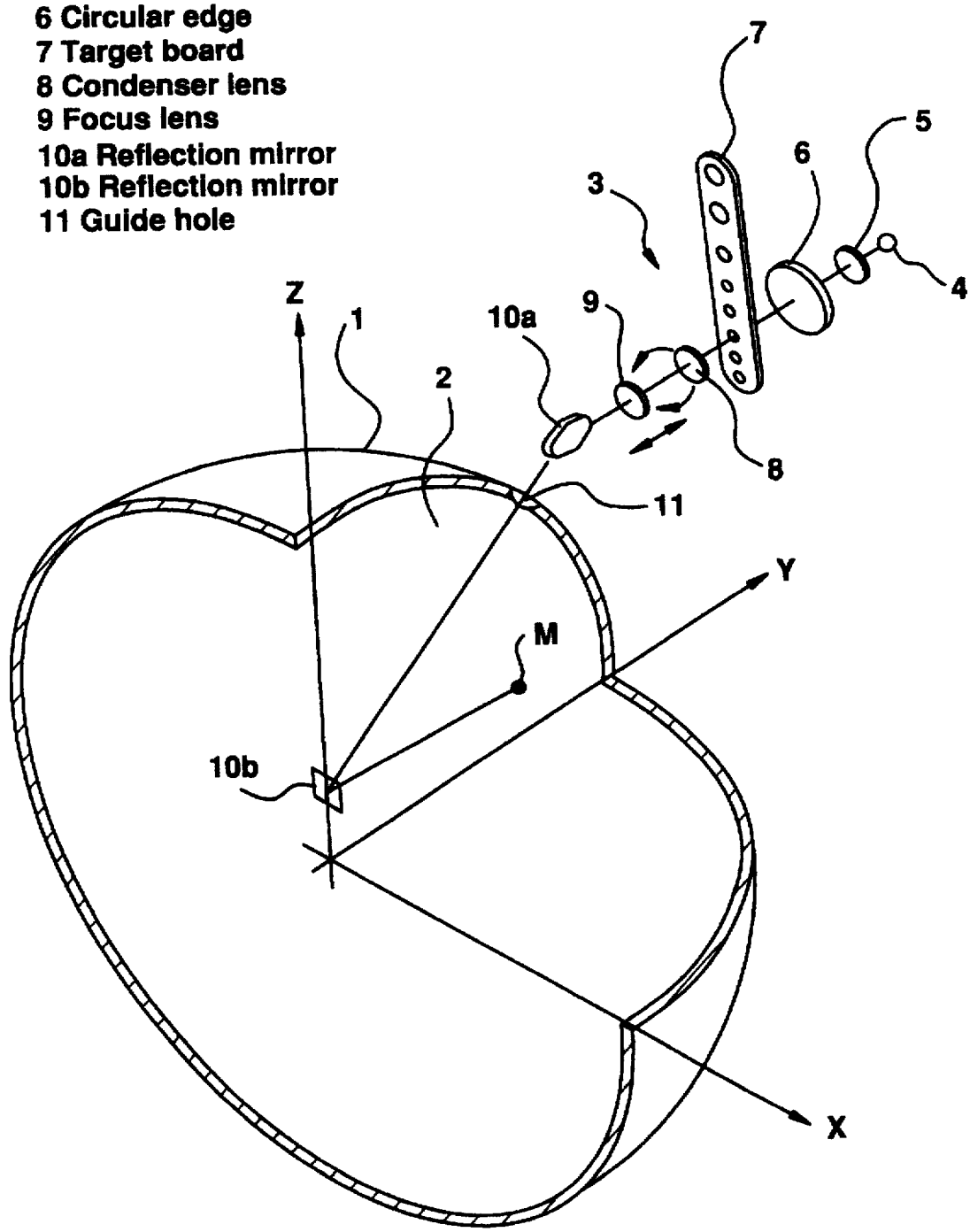
FIG. 1 is a perspective view of a perimetric measuring arrangement for use with this invention.

FIG. 1 is a perspective view of a perimetric measuring arrangement for use with this invention. As shown in FIG. 1, the arrangement includes a half spherical dome 1 having a projecting screen 2 on an inside surface. The dome is approximately 30 cm in radius. In FIG. 1, the patient views the projection screen 2 from the left. A projecting optical system 3 is mounted on a backside of the dome 1.

The projecting optical system 3 includes an illuminating light 4, a condenser lens 5, a circular edge 6, a target board 7, a condenser lens 8, a focus lens 9, a reflection mirror 10a and a reflection mirror 10b. The reflection mirror 10b is mounted inside of the dome 1. The projecting optical system 3 projects light through a guide hole 11 to form a target, that is, an image, M at a predetermined position on the projecting screen 2. As will be described in detail below, a sequence of different targets M are projected on the screen 2 and the patient tells the apparatus and/or a technician whether or not he or she senses the target. This physical arrangement of the projecting optical system is similar to a perimetric measuring apparatus described in Japanese Patent Application No. 61-282475 entitled "Perimeter" and filed Nov. 27, 1986.

The circular edge 6 has two polarizing filters (or a neutral density or ND filters) and a shutter which changes the luminance, or the "intensity of light," of the target M by changing an angle of one polarizing filter with respect to the other polarizing filter. The shutter opens to start the projecting of the target and it closes to and the projecting. The target board 7 has a number of apertures of different sizes to set the target size.

Figure 2:
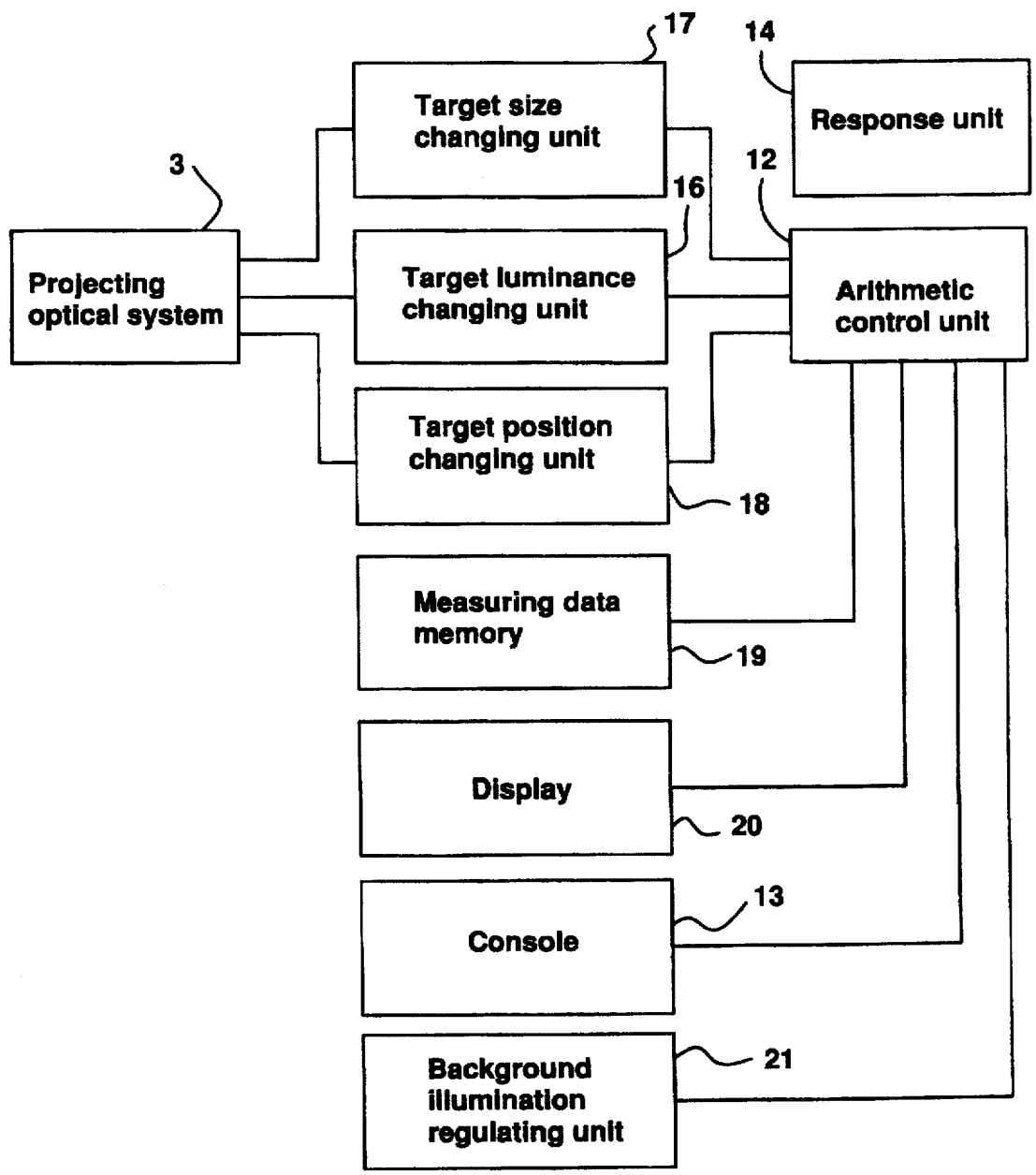
FIG. 2 is a block diagram of a perimetric measuring apparatus in accordance with this invention.

The components that control the arrangement depicted in FIG. 1 are shown in FIG. 2. The control operations, to be described in detail below, are an important part of this invention.

Referring to FIG. 2, the perimetric measuring apparatus includes an arithmetic control unit 12 having a CPU and other electronic circuitry such as memories, registers and the like. The arithmetic control unit 12 controls several other components based on an instruction from a console 13, a response from a response unit 14, and a perimetric measuring program.

When a receptive field measuring program is selected by an instruction from the console 13, the arithmetic control unit 12 reads the receptive field measuring program from a program memory (not shown), and implements the receptive field measuring program, as described below.

In one program mode the luminance of the target M is varied. To vary the luminance of the target, the arithmetic control unit 12 outputs a target luminance changing signal to a target luminance changing unit 16 to vary the luminance by changing an angle between the two polarizing filters of circular edge 6.

The arithmetic control unit 12 outputs a signal to open the shutter of the circular edge 6 to start the projection of the target, and outputs a signal to close the shutter to end projection of the target.

To change the size of the target, the arithmetic control unit 12 outputs a signal to a target size changing unit 17 to move the target board 7 up and down and thereby change the size of the light beam.

To change the position of the target, the arithmetic control unit 12 outputs a signal to a target position changing unit 18 to change the angle(s) of the mirror 10b and thereby change the position of the target on the screen 2.

The response unit 14 receives responses from the patient. A measuring data memory 19 stores data corresponding to a response from the response unit 14. When a measurement ends, the arithmetic control unit 12 instructs a display 20 to display the results of the measurement.

The arithmetic control unit 12 and the target luminance changing unit 16 together set an initial luminance of the stimulus.

The arithmetic control unit 12 also outputs a background luminance regulating signal to the background illumination regulating unit 21 based on instructions from the console 13. A background illumination regulating unit 21 regulates the luminance of a background on the projecting screen 2 by adjusting the luminance of a light (not shown) for illuminating the projecting screen 2. Generally, when the background is dark, the receptive field of the patient (corresponding to the measured area) is large and it is possible to perform an effective measurement. When the background is bright, the receptive field of the patient gate smaller and it is possible to perform a precise measurement.

In this particular embodiment, the target board 7 has eight circular apertures (circular holes) to permit use of eight possible target sizes. The circular apertures are designated –II, –I, O, I, II, III, IV, V (Goldmann targets). Professor Goldmann adopted the notation of Roman numerals to designate standard sizes for a dome radius of 30 cm.

The Roman numerals correspond to solid angles as follows:

$-II=(1/256)mm^2$ at 30 cm (average diameter, 0.012 degree)

$-I=(1/64)mm^2$ at 30 cm (average diameter, 0.025 degree)

$-O=(1/16)mm^2$ at 30 cm (average diameter, 0.05 degree)

$I=(1/4)mm^2$ at 30 cm (average diameter, 0.11 degree)

$II=(1)mm^2$ at 30 cm (average diameter, 0.22 degree)

$III=(4)mm^2$ at 30 cm (average diameter, 0.43 degree)

$IV=(16)mm^2$ at 30 cm (average diameter, 0.86 degree)

$V=(64)mm^2$ at 30 cm (average diameter, 1.72 degree)

Figure 3:
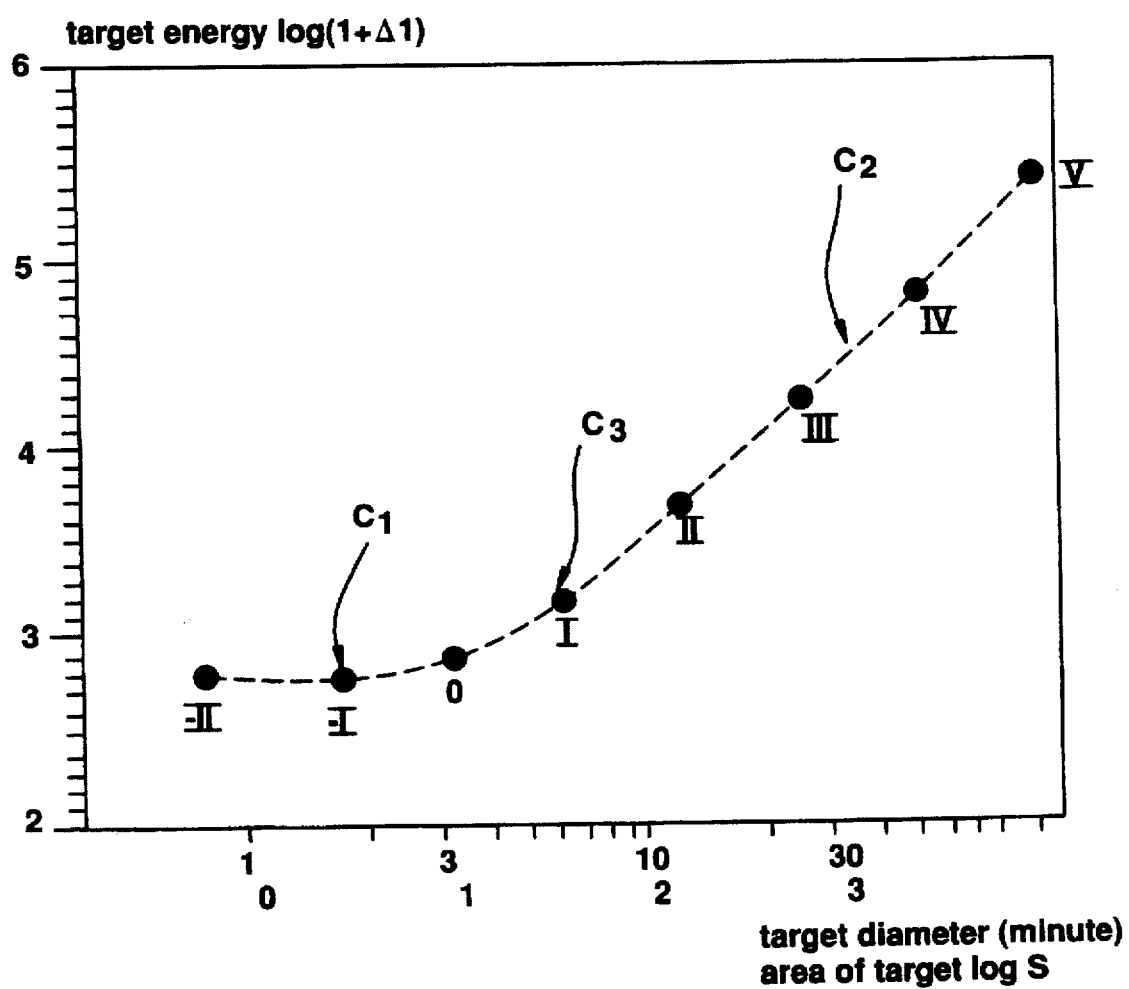
FIG. 3 is a graph for explaining characteristics of a receptive field of an eye.

FIG. 3 shows a threshold curve for a normal patient. In FIG. 3, there is a complete spatial summation area C1, a non-spatial summation area C2, and an incomplete spatial summation area C3.

The complete spatial summation area C1 is an area where the energy (intensity times area) of the target corresponding to a threshold level is constant even if the size of the target is changed, and where the luminance of the target corresponding to the threshold level increases in proportion to the size of the target. In other words, the complete spatial summation area C1 is an area where the size of the target is smaller than the size of a receptive field at that point. Receptive field is a unit area which is responsive to light.

The non-spatial summation area C2 is an area where the energy (luminance times area) of the target corresponding to the threshold linearly increases in proportion to the size of the target.

The incomplete spatial summation area C3 is between the complete spatial summation area C1 and the non-spatial summation area C2, and is an area where the energy (luminance times area) of the target corresponding to the threshold increases in proportion to target size along a curve.

In FIG. 3, points –II and –I are in the complete spatial summation area C1. Points II, III, IV, and V are in the non-spatial summation area C2. Points O and I are in the incomplete spatial summation area C3. The size of the receptive field change based on the patient.

Figure 4:
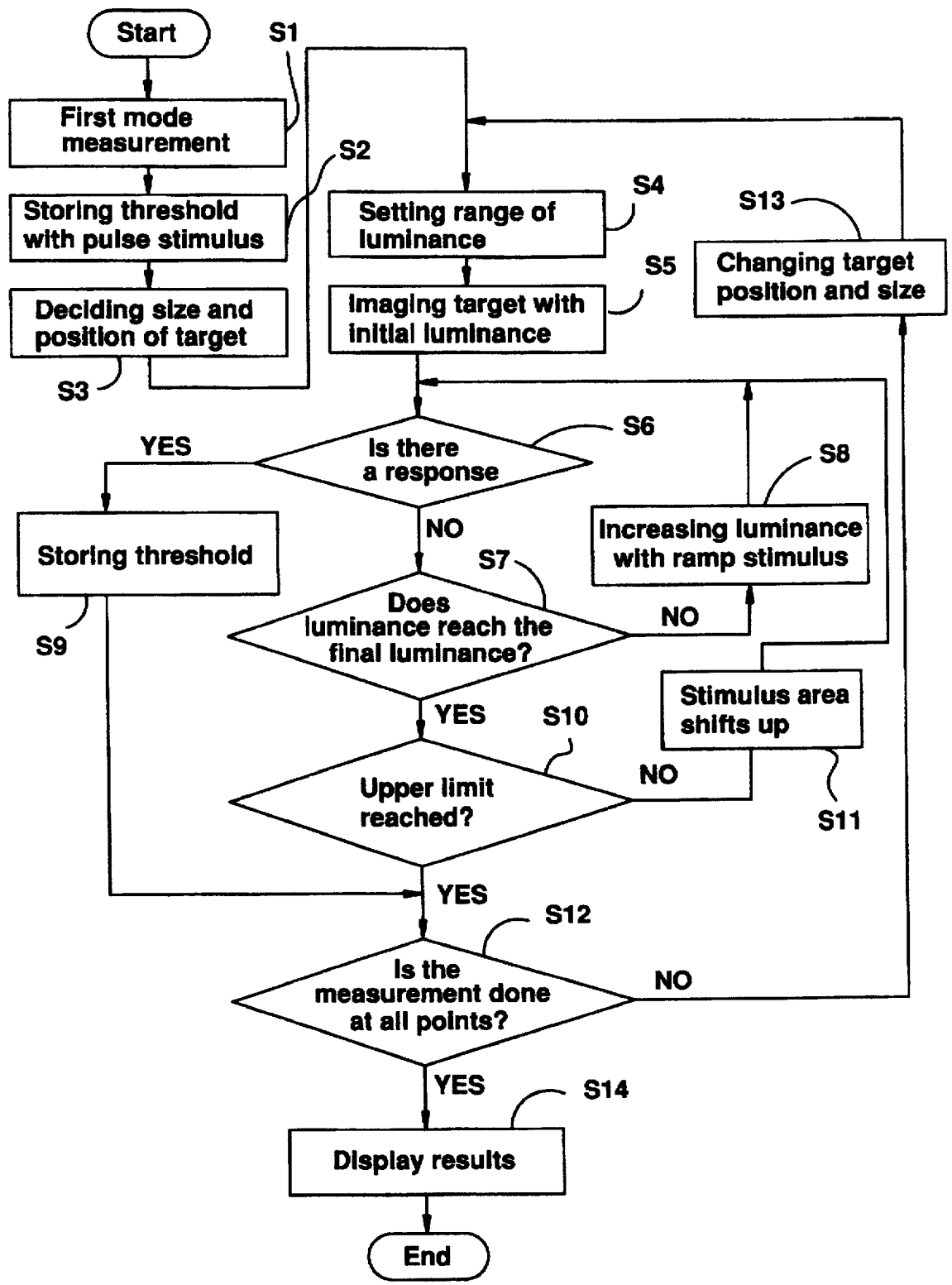
FIG. 4 is a flow chart of the processing of perimetric measurements performed by this invention.

FIG. 4 is a flow chart of the processing of a perimetric measurement performed by this invention.

The perimetric measuring apparatus of the invention includes a general perimetric measuring program (such as a static stimuli measuring program and the like) and a receptive field measuring program.

The general perimetric measuring program provides a pulse stimulus to the patient and then obtains characteristic (s) of the Y ganglion cells as a result of the pulse stimulus. The general perimetric measuring program is well-known and accordingly a detailed description thereof is not provided here.

Figure 5:
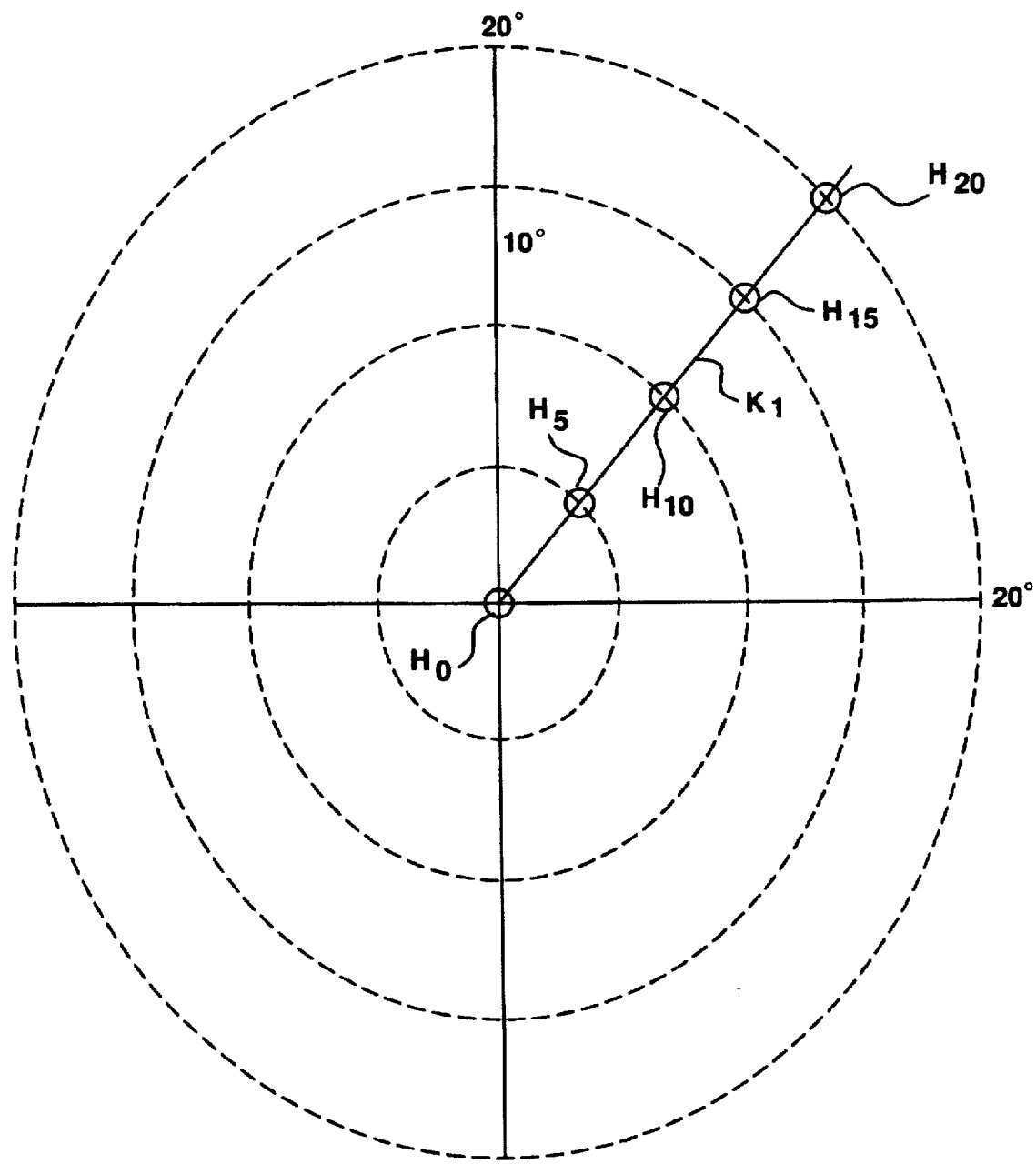
FIG. 5 shows positions of targets.

The receptive field measuring program uses target sizes –II through V. The receptive field measuring program generates stimuli at points H0, H5, H10, H15, and H20 at eccentric angles 0°, 5°, 10°, 15°, and 20° along a 45° line K1 (on the temporal side), as shown in FIG. 5.

The perimetric measuring apparatus performs the receptive field measuring program when it is selected. Referring to FIG. 4, a first mode of measurement is performed in step S1. The first mode of measurement is performed to give the patient a pulse stimuli at the complete spatial summation area C1 (target sizes –II and –I) and the non-spatial summation area C2 (target sizes II to V) at a threshold level stimulus.

In this embodiment, the first mode measurement is performed with target sizes III and –I. The position of the target is H0 in FIG. 5.

In step S2, measuring data memory 19 stores the threshold measured in step S1.

In step S3, sizes of the target and positions of the target for a second mode of measurement are determined. For example, target sizes of V, IV, III, II, I, ), –I, –II are used in order. Random positions of the targets are determined using a random number to prevent the patient from predicting the position of the target.

In step S4, a range of luminance (intensity) of the targets for the second mode of measurement is set according to the threshold level measured in step S1. In this embodiment, this setting is performed in accordance with the chart of FIG. 6. For example, if the threshold level is D10, when a size –I target is used, the initial luminance D1 of the target is the following:

$$D1=D10-3\ dB$$

This initial luminance is thus set as D1, when a size –I target is used at the position H0=0°.

The final luminance is set as D1+10 dB. The luminance of the target at the position H0 is thus varied from D1 to D1+10 dB linearly as a ramp stimulus. An upper limit of target luminance is set at a value of D1+30 dB.

This initial luminance is set as D1+6 dB when the size –II target is used at a position H0=0°. In the same manner, in the case of the size –II target at the positions 5°, 10°, . . . initial luminance are D1–2 dB, D1–4 dB. . . .

When using other –I size targets, initial luminances are set in accordance with FIG. 6 and the final luminances and upper limits are set in the above manner.

When using target sizes I through V, initial luminances of targets are decided according to the threshold level of target size III. Suppose the threshold is D20, an initial luminance D2 of the target is D20−3 dB. This initial luminance D2 is for a size III target at position H0=0°. The final luminance of the target is D2+10 dB. An upper limit of the stimulus is D2+30 dB.

In step S5, a target is generated on the projecting screen. The generated target has a size of V, IV, III, II, I, O, −I, −II. The target appears randomly at the position determined in step S3.

For example, choosing target size V, the target will appear at one of the points H0 to H20 shown FIG. 5. At this time, the initial luminance of the target is D2.

In step S6, it is judged whether or not there is a response from the patient. If the patient does not respond to the stimulus, the processing proceeds to step S7. If the patient does respond to the stimulus, the processing goes on to step S9.

In step S7, it is judged whether or not the luminance of the target reaches the final luminance. If the luminance of the target reaches the final luminance, the processing goes on to step S10. If not, the processing goes on to step S8.

In step S8, the luminance of the target increases, or ramps up, continuously.

Figure 7:
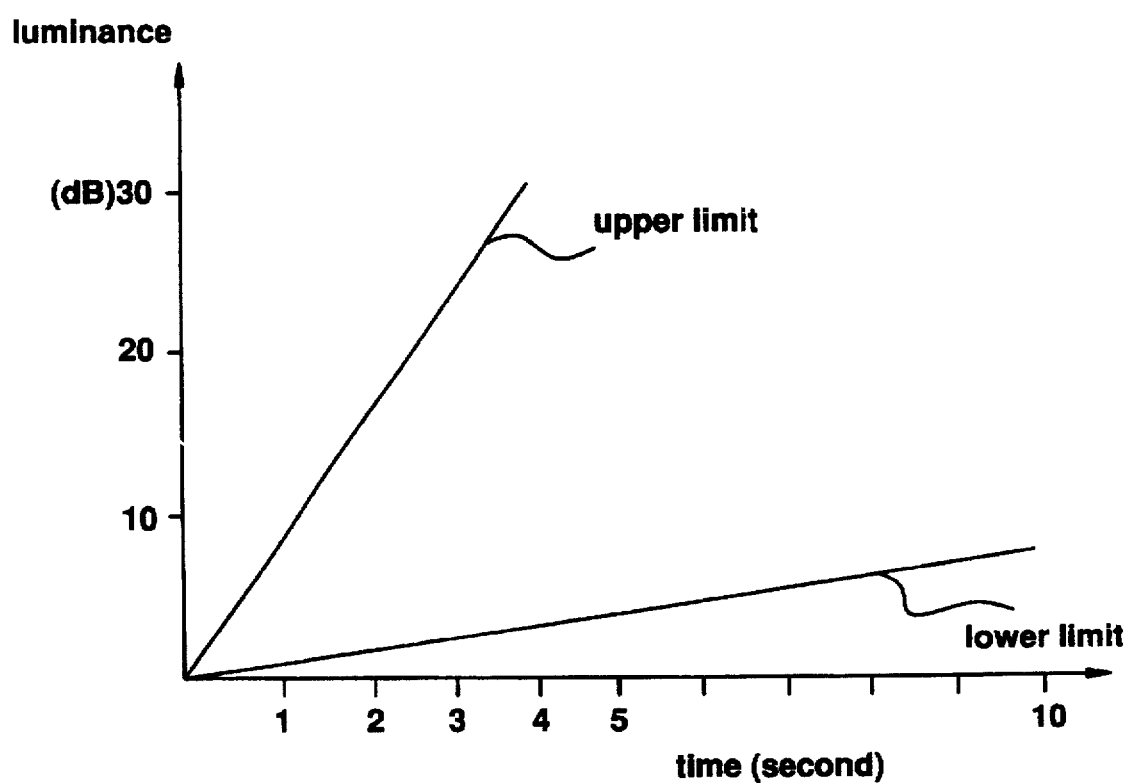
FIG. 7 is a graph showing a rate of change of luminance of a target.

Referring to FIG. 7, it is preferred that this changing rate of luminance be between 0.7 dB/second (a 10 dB charge during 14 seconds) and 7.5 dB/second (a 30 dB change during 4 seconds). As used herein, the unit dB means:

$$10*10 \log(\text{luminance of target/standard luminance})$$

where the standard luminance is 10,000 apostilbs (asb).

If the changing rate is too slow, there is some time lag between noticing the target and responding. If measurement takes a long time, the patient blinks and does not keep a fixed gaze and then the target looks like a pulse stimulus to the patient. If the changing rate is too fast, the target looks like a pulse stimulus to the patient. Thus, in this embodiment, a 1.25 dB/second changing rate of the luminance is selected.

Steps S6 through S8 are repeated until the patient responds. The changing area is shifted up every time steps S6 through S8 are repeated. For example, referring to FIG. 21, suppose a stimulus is from D2 to D2+10 dB at an initial stage, the stimulus is set to D2+3 dB to D2+13 dB after one performance of steps S6 to S8.

This measurement is the second mode of measurement.

If there is a response from the patient, the processing goes from step S6 to step S9. In step S9, the measuring data memory 19 stores the luminance of the target as the threshold upon receiving a response from the patient.

If there is no response from the patient and the luminance of the target reaches the final luminance of the stimulus area, the processing goes from step S7 to step S10. In step S10, it is judged whether or not the set final luminance reaches the upper limit (D2 plus 40 dB).

If the set final luminance does not reach the upper limit (D2 plus 40 dB), the stimulus area is shifted up in step S11. This means that the stimulus area set in step S4 is shifted up. This shift means that, for example, the new initial luminance of the stimulus area is set to be at a level D2+3 dB, as shown in FIG. 21. In other words, 3 dB is added to the initial luminance of D2, and a new final luminance is set to be D2+10 dB+3 dB. Thus, a new stimulus area is set from D2+3 dB to D2+10 dB+3 dB.

A target with this new stimulus area is made to appear. If there is no response with this new stimulus area, an additional new stimulus area is once again set in step S11. In this case, the additional new stimulus area is set from D2+6 dB to D2+16 dB.

Then, steps S6 through S8, step S10 and step S11 are repeated until a response from the patient is received. If the set final luminance reaches the upper limit (D2 plus 40 dB), the processing proceeds to step S12.

In step S12, it is judged whether or not measurements at all points are finished. If not, the processing goes on to step S13. If all points are finished, the processing goes on to step S14.

In step S13, the position and the size of target M are changed. This changing of the target position is performed by changing the orientation of the reflection mirror 10b.

Changing of the target size is performed by changing the aperture being used by sliding the target board 7 up and down to line up the desired aperture along the optical axis.

In step S14, after the above processing, the results of the measurement are displayed. The arithmetic control unit 12 classifies the thresholds with approximately constant energy (that is, the whole energy, or intensity times target area) at the same position (having various sizes) as a group of the complete spatial summation area C1.

The arithmetic control unit 12 classifies the thresholds with approximately constant luminance (energy per unit area) at the same position (having various sizes) as a group of the non-spatial summation area C2.

The arithmetic control unit 12 classifies the thresholds without approximately constant energy or luminance (energy per unit area) at the same position (having various sizes) as a group of the incomplete spatial summation area C3.

Figures 8A, 8B:
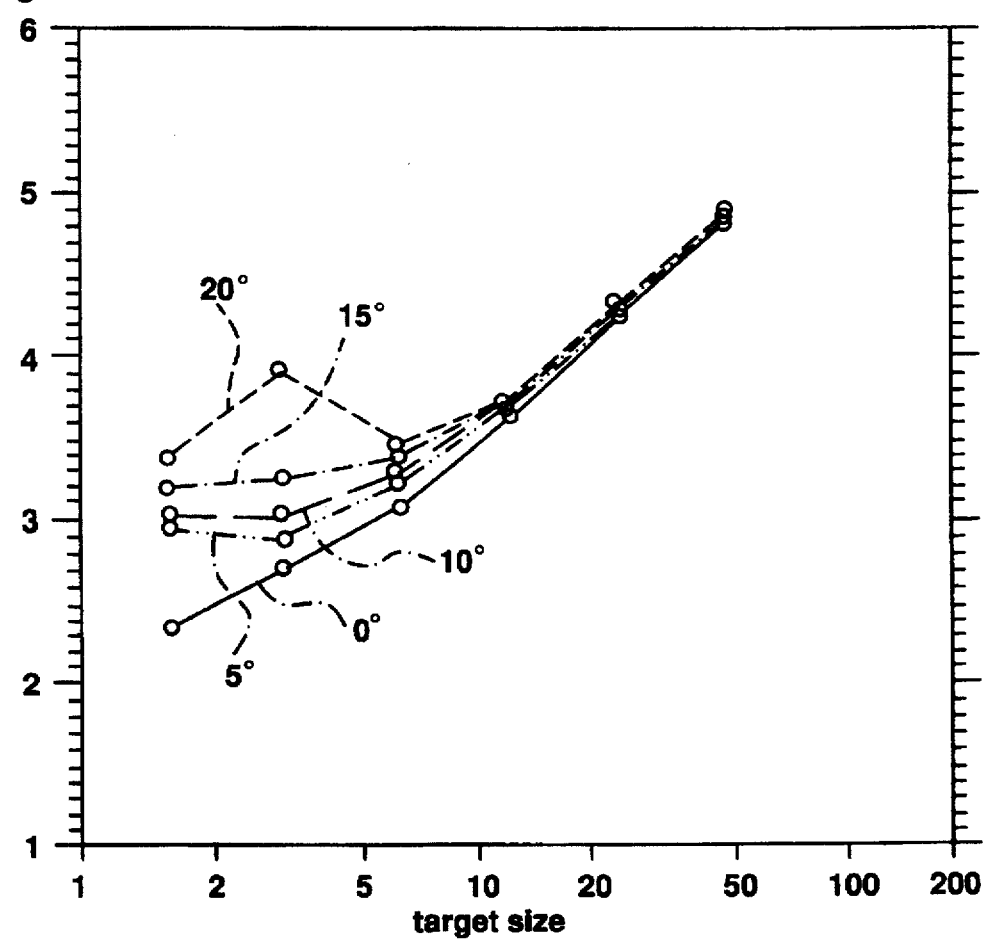
FIG. 8(a) is a graph showing characteristics of Y ganglion cells of a patient α with pulse stimulus.
FIG. 8(b) is a chart showing characteristic data of Y ganglion cells of a patient α with pulse stimulus.

FIGS. 8(a) and 8(b) show measured threshold characteristics of a patient α (a normal person) with a pulse stimulus. In FIG. 8(a), the horizontal axis corresponds to the diameter of the target, and the vertical axis corresponds to the luminance of the target.

Figures 9A, 9B:
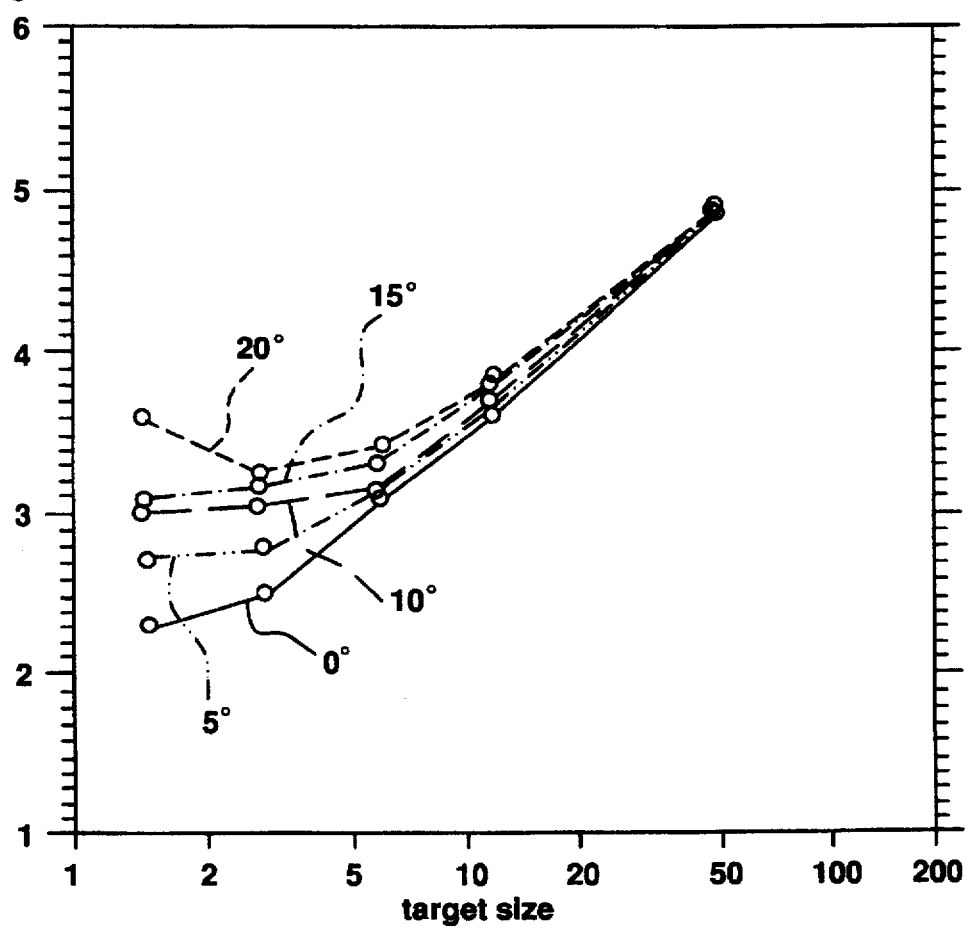
FIG. 9(a) is a graph showing characteristic of X ganglion cells of a patient α with ramp stimulus.

FIGS. 9(a) and 9(b) show measured threshold characteristics of the patient (normal person) with a ramp stimulus at a rate of 1.25 dB/second, which corresponds to responses of X ganglion cells.

FIG. 10 shows a flow chart for another embodiment. In this embodiment, the target is imaged with a ramp stimulus at a rate of 7.5 dB/second (changing the luminance 30 dB during 4 seconds).

In this embodiment, step S10 and step S11 of FIG. 4 are not required. The other steps in FIG. 10 are the same as in FIG. 4.

FIGS. 11(a) and 11(b) show measured threshold characteristics of the patient α (a normal person) with a ramp stimulus at a rate of 7.5 dB/second, which corresponds to responses of X ganglion cells.

FIGS. 12(a) and 12(b) show measured threshold characteristics of the patient α (a normal person) with a ramp stimulus at a rate of 15 dB/second (changing the luminance 30 dB during 2 seconds), which corresponds to responses of X ganglion cells.

FIGS. 13(a) and 13(b) show measured threshold characteristics of the patient α (a normal person) with a ramp stimulus at a rate of 3.75 dB/second (changing the luminance 30 dB during 8 seconds), which corresponds to responses of X ganglion cells.

FIGS. 14(a) and 14(b) show measured threshold characteristics of the patient α (a normal person) with a ramp stimulus at a rate of 3.0 dB/second (changing the luminance 30 dB during 10 seconds), which corresponds to responses of X ganglion cells.

FIGS. 15(a) and 15(b) show measured threshold characteristics of a patient β (a normal person) with a pulse stimulus.

FIGS. 16(a) and 16(b) show measured threshold characteristics of the patient β (a normal person) with a ramp stimulus at a rate of 15 dB/second, which corresponds to responses of X ganglion cells.

FIGS. 17(a) and (b) show measured threshold characteristics of the patient β (a normal person) with a ramp stimulus at a rate of 7.5 dB/second (changing the luminance 30 dB during 4 seconds), which corresponds to responses of X ganglion cells.

FIGS. 18(a) and 18(b) show measured threshold characteristics of the patient β (a normal person) with a ramp stimulus at a rate of 3.75 dB/second (changing the luminance 30 dB during 8 second), which corresponds to responses of X ganglion cells.

FIGS. 19(a) and 19(b) show measured threshold characteristics of the patient β (a normal person) with a ramp stimulus at a rate of 1.25 dB/second (changing the luminance 10 dB during 8 seconds), which corresponds to responses of X ganglion cells.

FIGS. 20(a) and 20(b) show measured threshold characteristics of the patient β (a normal person) with a ramp stimulus at a rate of 1.25 dB/second (changing the luminance 10 dB during a seconds), which corresponds to responses of X ganglion cells.

The arithmetic control unit 12 judges whether or not there is an abnormal portion of the patient's eye based on the measured data and displays the results of the measurements.

This judgment is performed by the following techniques.

The first technique determines whether or not there is any deviation between an energy of a threshold with a target size of 0, I or II (bigger than the receptive field) and an energy of a threshold with a target size of –I or –II (smaller than the receptive field).

In the case of a normal person, there is no or only a slight deviation between these different energy levels. However, if the patient has an abnormal condition, there is some significant devication between these different energy levels. In the case of a normal person, if the target size is changed in the complete spatial summation area C1, the threshold energy does not change strikingly.

In the case of a person with an abnormal condition, if the target size is changed in the complete spatial summation area C1, the threshold energy changes strikingly.

A second technique is to determine whether or not (1) an energy per unit area of the threshold with the lowest threshold of the target size larger than the receptive field is higher than (2) an energy per unit area of another threshold in the non-spatial summation area C2. In other words, the technique is to determine whether or not threshold energies per unit area in the non-spatial summation area C2 are constant. In the case of a normal person, threshold energies per almost constant. However, in the case of a person with an abnormal condition, there is a threshold energy per unit area with some significant deviation from another one of the thresholds. In the case of a normal person, threshold energies in the non-spatial summation area C2 change linearly. However, in the case of a person with an abnormal condition, the energy of the thresholds in the non-spatial summation area C2 do not change linearly.

Using techniques such as described above, the arithmetic control unit 12 makes a judgment based on the measured data as to whether or not there is an abnormal portion of the eye.

Generally, the patient can keep his or her gaze at a fixed point for 5 to 7 seconds (the maximum fixation time) without blinking. It is preferred that the time from making the target appear until response be shorter than the maximum fixation time. If the gaze of the patient changes, the patient might perceive the ramp stimulus as a pulse stimulus and the measurement results would incorrectly correspond to characteristics of the Y ganglion cells instead of characteristics of the X ganglion cells.

On the other hand, if the rate of change of the target luminance is too fast, the patient might perceive a ramp stimulus as a pulse stimulus. This is also no good.

The target appearing time is typically set between 4 seconds and 14 seconds. Preferably, the patient responds at half or just before half of the target appearing time. A more preferred target appearing time is between 5 seconds and 9 seconds.

If the rate of change of the target luminance is too slow, the patient can not keep his or her gaze at the fixation point.

There is thus an appropriate range for the rate of changing the target luminance for obtaining characteristics of the X ganglion cells. More particularly, the preferably range for the rate of changing the target luminance is from 0.7 dB/second (10 dB/14 seconds) to 7.5 dB/second (30 dB/4 seconds). The upper value of 7.5 dB/second (30 dB/4 seconds) is decided that a changing density area with one filter (30 dB) divided by a minimum target appearing time (4 seconds). The lower limit of 0.7 dB/second (10 dB/14 seconds) is based on one third the changing density area with one filter (30 dB) divided by a target appearing time which is two times the maximum fixation time (14 seconds).

If the patient and technician are able to withstand an increasing number of measurements, a changing density area can be set to less than the area 10 dB.

The starting of luminance of the target is set at a time to keep the response time within the maximum fixation time and to project the desired ramp stimulus.

As indicated in FIG. 6, in the complete spatial summation area C1, the starting luminance of the target is higher as the size of the target gets smaller. In the complete spatial summation area C1, the energy (a luminance times an area) of the target at a starting luminance is constant in spite of the size of the target. Also, in the complete spatial summation area C1, the starting luminance of the target is higher as the position of the target gets farther from 0 degrees.

In the complete spatial summation area C1, the energy (a luminance times an area) of the target at the starting luminance is higher as the angle from the center increases. Because the sensitivity of the nerve cells gets lower as the position of the target gets farther from the center, when targets at different positions (different angles from the direction of fixation) are measured, the size of the target and the rate of change of the luminance of the target are set to an appropriate value for measuring.

In the above described embodiments, the starting luminance of the target and the size of the target are set according to three factors: (1) the threshold measured during the first, or pulse, mode, (2) the target size, and (3) the target position. However, it is possible to set the starting luminance based on two factors—the threshold measured during the first mode and the target size, or the threshold measured during the first mode and the target position. Also, the starting luminance of the target and the size of the target can be set according to a threshold determined in prior measurements (such as general perimetric measurements of Y ganglion cells or measurements of X ganglion cells).

In this invention, the appropriate starting luminance of the target and the size of the target are set according to the above-described factors to measure characteristics of X ganglion cells. Because the invention makes it possible to measure characteristics of X ganglion cells, the invention makes it possible to find certain defects at an early stage.

The invention is not limited to the specific embodiments and examples set forth above. The true scope of the invention is set forth by the following claims.

What is claimed is:

1. An apparatus for measuring a visual field of a patient, comprising:

a response device for measuring a response of the patient;

a target presenting device for presenting a target for viewing by the patient, the target presenting device having a first mode and a second mode, the first mode presenting a target with a pulse stimulus for measuring a characteristic of Y ganglion cells, the second mode presenting a target with a ramp stimulus for measuring a characteristic of X ganglion cells, in the second mode, the target presenting device presenting the target at an initial stimulus based on a response received from the patient in the first mode.

2. The apparatus according to claim 1, wherein the target presenting device generates a sequence of targets for determining characteristics of ganglion cells.

3. The apparatus according to claim 2, wherein the target presenting device generates a target having a size in a complete spatial summation region and generates a target having a size in a non-spatial summation region in the first mode.

4. The apparatus according to claim 1, further comprising a classifying means for classifying results based on a whole energy of stimulus and an intensity of stimulus in the second mode.

5. The apparatus according to claim 1, further comprising a classifying means for classifying results in the second mode into a group of constant whole threshold energy as a complete spatial summation group, or into a group of constant threshold energy per unit area as a non-spatial summation group.

6. An apparatus for measuring a visual field of a patient, comprising:

a target presenting device for presenting targets of various sizes with a ramp stimulus for viewing by the patient;

a stimulus area setting device for setting a stimulus area in accordance with a size set by the target presenting device;

a response device for measuring a response of the patient; and a memory for storing an intensity of stimulus and a target size corresponding to response received from the patient.

7. The apparatus according to claim 6, wherein the target presenting device generates a sequence of targets for determining characteristics of X ganglion cells.

8. The apparatus according to claim 6, further comprising a classifying means for classifying results of said ramp stimulus based on a whole energy of stimulus and an intensity of stimulus.

9. The apparatus according to claim 6, further comprising a classifying means for classifying results of said ramp stimulus into a group of constant whole threshold energy as a complete spatial summation group, or into a group of constant threshold energy per unit area as a non-spatial summation group.

10. An apparatus for measuring a visual field of a patient, comprising:

a target presenting device for presenting targets with a varying intensity of a ramp stimulus at desired positions for viewing by the patient;

a target size changing device for changing a size of targets generated by the target presenting device;

a stimulus area setting device for setting a stimulus area in accordance with a position of a target to be generated by the target presenting device;

a response device for measuring a response of the patient; and a memory for storing an intensity of stimulus and a target size corresponding to responses received from the patient.

11. The apparatus according to claim 10, wherein the target presenting device generates a sequence of targets of determining characteristics of X ganglion cells.

12. An apparatus for measuring a visual field of a patient, comprising:

a target presenting device for presenting targets with a varying intensity of a ramp stimulus at desired positions for viewing by the patient;

a target size changing device for changing a size of targets generated by the target presenting device;

a stimulus area setting device for setting a stimulus area in accordance with a position and size of a target to be generated by the target presenting device;

a response device for measuring a response of the patient; and a memory for storing an intensity of stimulus and a target size corresponding to responses received from the patient.

13. The apparatus according to claim 12, wherein the target presenting device generates a sequence of targets for determining characteristics of X ganglion cells.

14. The apparatus according to claim 13, further comprising detecting means for detecting an abnormal portion of the patient's eye based on whether or not (1) an energy per unit area of the threshold with the lowest threshold of the target size larger than a receptive field is higher than (2) an energy per unit area of another threshold in a non-spatial summation area C2.

15. An apparatus for measuring a visual field of a patient, comprising:

a target presenting device for presenting targets with a varying intensity of stimulus at desired positions for viewing by the patient;

a stimulus intensity changing device for changing the intensity of stimulus based on a position and size of a target generated by the target presenting device, the stimulus intensity changing device changing the intensity of the stimulus at a stimulus intensity changing rate which is slower than a response rate of Y ganglion cells and faster than a patient's fixation instability rate;

a response device for measuring the response of the patient; and a memory for storing an intensity of stimulus and a target size corresponding to response received from the patient.

16. The apparatus according to claim 15, wherein the target presenting device generates a sequence of targets for determining characteristics of ganglion cells.

17. The apparatus according to claim 16, wherein the stimulus intensity changing device changes the intensity of stimulus at a stimulus intensity changing rate between a lower limit of 3 dB/second and an upper limit of 7.5 dB/second.

18. The apparatus according to claim 16, wherein the stimulus intensity changing device changes the intensity of stimulus over a stimulus intensity changing term between 4 seconds and 14 seconds.

19. The apparatus according to claim 16, wherein the stimulus intensity changing device changes the intensity of stimulus over a stimulus intensity changing term between 5 seconds and 9 seconds.

20. The apparatus according to claim 16, wherein the stimulus intensity changing device changes the intensity of stimulus at a stimulus intensity changing rate between a lower limit of 0.7 dB/ second and an upper limit of 7.5 dB/second.

21. An apparatus for measuring a visual field of a patient, comprising:

a target presenting device for presenting targets of various sizes with a monotonically-increasing stimulus for viewing by the patient;

a stimulus area setting device for setting a stimulus area in accordance with a size set by the target presenting device;

a response device for measuring a response of the patient; and a memory for storing an intensity of stimulus and a target size corresponding to responses received from the patient.

22. An apparatus for measuring a visual field of a patient, comprising:

a target presenting device for presenting targets with a varying intensity of a monotonically-increasing stimulus at desired positions for viewing by the patient;

a target size changing device for changing a size of targets generated by the target presenting device;

a stimulus area setting device for setting a stimulus area in accordance with a position of a target to be generated by the target presenting device;

a response device for measuring a response of the patient; and a memory for storing an intensity of stimulus and a target size corresponding to responses received from the patient.

* * * * *